US010858433B2

(12) United States Patent
Zhang et al.

(10) Patent No.: US 10,858,433 B2
(45) Date of Patent: Dec. 8, 2020

(54) MONOCLONAL ANTIBODY AGAINST PD-1 AND APPLICATION THEREOF

(71) Applicants: TAIZHOU HANZHONG BIOPHARMACEUTICS, INC., Jiangsu (CN); AKESO BIOPHARMA, INC., Guangdong (CN)

(72) Inventors: Faming Zhang, Hubei (CN); Gan Xi, Hubei (CN); Ying Huang, Hubei (CN); Yu Xia, Guangdong (CN); Baiyong Li, Guangdong (CN); Zhongmin Maxwell Wang, Guangdong (CN)

(73) Assignees: Taizhou Hanzhong Biopharmaceutics, Inc., Taizhou (CN); Akeso Biopharma, Inc., Zhongshan (CN)

( * ) Notice: Subject to any disclaimer, the term of this patent is extended or adjusted under 35 U.S.C. 154(b) by 0 days.

(21) Appl. No.: 16/510,449

(22) Filed: Jul. 12, 2019

(65) Prior Publication Data
US 2019/0330347 A1 Oct. 31, 2019

Related U.S. Application Data

(63) Continuation of application No. PCT/CN2017/071125, filed on Jan. 13, 2017.

(51) Int. Cl.
*C07K 16/28* (2006.01)
*A61K 38/17* (2006.01)
*A61P 35/00* (2006.01)
*A61K 31/58* (2006.01)
*A61K 31/606* (2006.01)
*A61K 31/635* (2006.01)
*A61K 31/655* (2006.01)

(52) U.S. Cl.
CPC ...... *C07K 16/2818* (2013.01); *A61K 38/1774* (2013.01); *A61P 35/00* (2018.01); *A61K 31/58* (2013.01); *A61K 31/606* (2013.01); *A61K 31/635* (2013.01); *A61K 31/655* (2013.01); *A61K 38/1793* (2013.01)

(58) Field of Classification Search
None
See application file for complete search history.

(56) References Cited

U.S. PATENT DOCUMENTS

2016/0215059 A1 7/2016 Liu et al.

FOREIGN PATENT DOCUMENTS

| WO | 2009086320 | 7/2009 |
|----|------------|--------|
| WO | 2017019846 | 2/2017 |

OTHER PUBLICATIONS

WIPO, ISR for PCT/CN2017/071125, dated Oct. 18, 2017.
Kuo et al., "Neonatal Fc receptor and IgG-based therapeutics," mAbs, 2011, vol. 3, issue 5, pp. 422-430.
Saxena et al., "Advances in Therapeutic Fc Engineering - Modulation of IgG-Associated Effector Functions and Serum Half-life," Frontiers in Immunology, Dec. 2016, vol. 7, article 580, 11 pages.
Yeung et al., "Engineering Human IgG1 Affinity to Human Neonatal Fc Receptor Impact of Affinity Improvement on Pharmacokinetics in Primates," The Journal of Immunology, 2009, vol. 182, No. 12, pp. 7663-7671.
EPO, Office Action for EP Application No. 17891529.4, dated May 6, 2020.

*Primary Examiner* — Padmavathi Baskar
(74) *Attorney, Agent, or Firm* — Hodgson Russ LLP

(57) ABSTRACT

Provided is a monoclonal antibody against programmed death-1 (PD-1) or applications thereof, where the monoclonal antibody against PD-1 comprises a neonatal Fc Receptor (FcRn)-binding site having an amino acid sequence of SEQ ID NO: 5.

7 Claims, 9 Drawing Sheets
Specification includes a Sequence Listing.

| Antibody | Equilibrium disassociation constant (M) | Binding rate constant (1/Ms) | Binding rate constant Error | Disassociation rate constant (1/s) | Disassociation rate constant Error | Rmax Range |
|---|---|---|---|---|---|---|
| H2L2 | 2.70E-10 | 2.40E+05 | 4.52E+03 | 6.48E-05 | 8.97E-06 | 0.2973-0.6169 |
| H8L2 | 1.03E-10 | 5.18E+05 | 1.36E+04 | 5.35E-05 | 1.06E-05 | 0.3548-1.0526 |

| Time (h) | Female | | | | | Male | | | | |
|---|---|---|---|---|---|---|---|---|---|---|
| | 2F001 | 2F002 | 2F003 | Mean | SD | 2M001 | 2M002 | 2M003 | Mean | SD |
| 0 | BLLOQ | BLLOQ | BLLOQ | / | / | BLLOQ | BLLOQ | BLLOQ | / | / |
| 0.083 | 21.042 | 22.321 | 19.750 | 21.038 | 1.286 | 21.456 | 20.738 | 16.799 | 19.664 | 2.507 |
| 0.5 | 19.647 | 20.949 | 20.562 | 20.386 | 0.669 | 20.832 | 18.869 | 15.552 | 18.418 | 2.669 |
| 1 | 20.399 | 21.930 | 19.412 | 20.557 | 1.287 | 23.778 | 18.120 | 14.653 | 18.848 | 4.602 |
| 2 | 18.785 | 19.913 | 18.344 | 19.014 | 0.809 | 19.763 | 19.183 | 15.034 | 17.993 | 2.579 |
| 4 | 16.283 | 17.645 | 17.406 | 17.111 | 0.727 | 17.589 | 16.083 | 13.459 | 15.710 | 2.090 |
| 8 | 15.111 | 14.531 | 17.122 | 15.588 | 1.360 | 15.402 | 14.830 | 12.477 | 14.236 | 1.550 |
| 24 | 14.199 | 12.379 | 16.018 | 14.199 | 1.820 | 14.081 | 11.915 | 10.898 | 12.298 | 1.626 |
| 48 | 12.211 | 10.736 | 15.216 | 12.721 | 2.283 | 14.916 | 13.530 | 10.144 | 12.863 | 2.455 |
| 144 | 7.816 | 9.632 | 13.344 | 10.264 | 2.818 | 12.330 | 9.072 | 7.201 | 9.534 | 2.596 |
| 216 | 6.913 | 7.610 | 9.096 | 7.873 | 1.115 | 8.773 | 6.508 | 5.299 | 6.860 | 1.763 |

| Time (h) | Female | | | | | Male | | | | |
|---|---|---|---|---|---|---|---|---|---|---|
| | 3F001 | 3F002 | 3F003 | Mean | SD | 3M001 | 3M002 | 3M003 | Mean | SD |
| 0 | BLLOQ | BLLOQ | BLLOQ | / | / | BLLOQ | BLLOQ | BLLOQ | / | / |
| 0.083 | 41.269 | 54.197 | 53.307 | 49.591 | 7.221 | 58.729 | 25.366 | 44.087 | 42.727 | 16.723 |
| 0.5 | 42.043 | 50.905 | 49.391 | 47.446 | 4.748 | 54.306 | 26.127 | 46.694 | 42.376 | 14.577 |
| 1 | 45.104 | 57.663 | 52.232 | 51.666 | 6.299 | 56.874 | 29.788 | 48.446 | 45.035 | 13.863 |
| 2 | 42.736 | 59.548 | 50.522 | 50.935 | 8.414 | 55.484 | 29.153 | 42.630 | 42.422 | 13.167 |
| 4 | 32.389 | 45.291 | 42.719 | 40.133 | 6.829 | 45.426 | 29.277 | 38.147 | 37.617 | 8.088 |
| 8 | 31.168 | 44.824 | 37.592 | 37.861 | 6.832 | 43.286 | 28.877 | 34.568 | 35.577 | 7.257 |
| 24 | 25.038 | 35.214 | 31.669 | 30.640 | 5.165 | 35.426 | 26.926 | 33.644 | 31.999 | 4.483 |
| 48 | 24.511 | 34.493 | 29.873 | 29.626 | 4.996 | 34.894 | 28.257 | 31.762 | 31.638 | 3.328 |
| 144 | 20.966 | 25.218 | 22.870 | 23.018 | 2.130 | 25.044 | 22.856 | 23.753 | 23.884 | 1.100 |
| 216 | 19.794 | 20.579 | 18.815 | 19.663 | 0.989 | 24.871 | 17.126 | 19.503 | 20.500 | 3.968 |

Figure 9

| Time (h) | Female | | | | | Male | | | | |
|---|---|---|---|---|---|---|---|---|---|---|
| | 4F001 | 4F002 | 4F003 | Mean | SD | 4M001 | 4M002 | 4M003 | Mean | SD |
| 0 | BLLOQ | BLLOQ | BLLOQ | / | / | BLLOQ | BLLOQ | BLLOQ | / | / |
| 0.083 | 168.622 | 181.695 | 222.556 | 190.958 | 28.135 | 212.165 | 202.114 | 184.324 | 199.534 | 14.099 |
| 0.5 | 180.423 | 189.465 | 217.407 | 195.765 | 19.280 | 200.985 | 204.463 | 196.901 | 200.783 | 3.785 |
| 1 | 171.584 | 180.131 | 227.327 | 193.014 | 30.022 | 213.926 | 129.091 | 200.903 | 181.307 | 45.687 |
| 2 | 162.088 | 158.081 | 195.920 | 172.030 | 20.786 | 159.397 | 171.065 | 162.022 | 164.161 | 6.121 |
| 4 | 129.262 | 141.646 | 166.375 | 145.761 | 18.896 | 147.036 | 164.261 | 148.131 | 153.143 | 9.644 |
| 8 | 109.762 | 130.214 | 154.920 | 131.632 | 22.612 | 144.861 | 164.234 | 141.027 | 150.041 | 12.440 |
| 24 | 99.563 | 116.381 | 131.541 | 115.828 | 15.996 | 139.223 | 153.140 | 118.217 | 136.860 | 17.581 |
| 48 | 102.600 | 101.538 | 128.206 | 110.781 | 15.100 | 103.992 | 113.076 | 101.747 | 106.272 | 5.999 |
| 144 | 68.168 | 75.714 | 93.658 | 79.180 | 13.094 | 79.281 | 61.980 | 85.163 | 75.475 | 12.051 |
| 216 | 63.303 | 63.073 | 89.478 | 71.951 | 15.179 | 77.849 | 68.156 | 79.443 | 75.149 | 6.109 |

Figure 10

| Time (h) | Female | | | | | Male | | | | |
|---|---|---|---|---|---|---|---|---|---|---|
| | 1F001 | 1F002 | 1F003 | Mean | SD | 1M001 | 1M002 | 1M003 | Mean | SD |
| 0 | BLLOQ | BLLOQ | BLLOQ | / | / | BLLOQ | BLLOQ | BLLOQ | / | / |
| 0.083 | 323.851 | 211.543 | 252.755 | 262.716 | 56.813 | 255.966 | 364.165 | 386.764 | 335.632 | 69.912 |
| 0.5 | 263.121 | 208.089 | 227.314 | 232.841 | 27.929 | 248.995 | 335.200 | 349.019 | 311.071 | 54.202 |
| 1 | 298.671 | 241.494 | 249.499 | 263.221 | 30.960 | 243.824 | 289.423 | 354.839 | 296.029 | 55.802 |
| 2 | 256.607 | 178.398 | 204.337 | 213.114 | 39.836 | 230.920 | 296.360 | 290.313 | 272.531 | 36.163 |
| 4 | 210.804 | 157.444 | 178.245 | 182.164 | 26.893 | 197.774 | 292.110 | 256.715 | 248.866 | 47.655 |
| 8 | 203.407 | 162.388 | 155.066 | 173.620 | 26.055 | 193.104 | 315.456 | 268.494 | 259.018 | 61.724 |
| 24 | 151.595 | 129.710 | 131.365 | 137.557 | 12.186 | 148.798 | 236.325 | 230.304 | 205.140 | 48.893 |
| 48 | 153.499 | 111.356 | 104.802 | 123.219 | 26.427 | 146.723 | 185.313 | 190.617 | 174.218 | 23.958 |
| 144 | 121.662 | 89.144 | 81.140 | 97.315 | 21.461 | 104.556 | 136.766 | 130.371 | 123.898 | 17.053 |
| 216 | 98.221 | 96.450 | 86.855 | 93.842 | 6.115 | 93.563 | 148.813 | 115.229 | 119.201 | 27.839 |

Figure 11

| Groups | Animal | t₁/₂ (h) | Animal | t₁/₂ (h) |
|---|---|---|---|---|
| 1 mg/kg | 2F001 | 169.02 | 2M001 | 233.86 |
| | 2F002 | 308.65 | 2M002 | 159.49 |
| | 2F003 | 248.30 | 2M003 | 184.99 |
| | N | 3 | N | 3 |
| | Mean | 241.99 | Mean | 189.45 |
| | SD | 70.03 | SD | 32.42 |
| 3 mg/kg | 3F001 | 536.79 | 3M001 | 248.13 |
| | 3F002 | 224.72 | 3M002 | 235.85 |
| | 3F003 | 246.35 | 3M003 | 240.84 |
| | N | 3 | N | 3 |
| | Mean | 335.95 | Mean | 241.61 |
| | SD | 174.26 | SD | 6.18 |
| 10 mg/kg | 4F001 | 248.51 | 4M001 | 203.33 |
| | 4F002 | 243.53 | 4M002 | 141.08 |
| | 4F003 | 312.98 | 4M003 | 464.12 |
| | N | 3 | N | 3 |
| | Mean | 268.34 | Mean | 269.51 |
| | SD | 38.74 | SD | 171.38 |
| 10 mg/kg Wild-type | 1F001 | 262.08 | 1M001 | 264.17 |
| | 1F002 | 249.34 | 1M002 | 177.68 |
| | 1F003 | 218.56 | 1M003 | 172.15 |
| | N | 3 | N | 3 |
| | Mean | 243.33 | Mean | 204.67 |
| | SD | 22.37 | SD | 51.61 |

Figure 12

MONOCLONAL ANTIBODY AGAINST PD-1 AND APPLICATION THEREOF

CROSS-REFERENCE TO RELATED APPLICATIONS

This application is a continuation of International Application No. PCT/CN2017/071125, filed Jan. 13, 2017, the entire disclosure of which is incorporated herein by reference.

FIELD

The present disclosure relates to the field of immunology and antibody engineering, in particular to a monoclonal antibody against programmed death-1 (PD-1) and application thereof.

BACKGROUND

Currently, there is still a need for a method of prolonging the serum half-life of Immunoglobulin G (IgG)-like antibody (especially naturally occurring IgG-like antibody) and increasing the binding affinity of the IgG-like antibody to Neonatal Fc Receptor (FcRn).

Programmed death factor 1 (PD-1) (also known as CD279, Gene ID: PDCD1, Genebank accession No: NP_005009), as an inhibitory member of the immunoglobulin superfamily homologous to CD28, is a cell surface receptor critical in the regulation of balance between stimulatory and inhibitory signals in the immune system as well maintenance of peripheral tolerance. PD-1 is a monomeric type I transmembrane protein, consisting of an immunoglobulin variable region-like extracellular domain and a cytoplasmic domain with an immunoreceptor tyrosine-based inhibition motif (ITIM) and an immunoreceptor tyrosine-based switch motif (ITSM). The expression of PD-1 is inducible on T cells, B cells, natural killer (NK) cells and monocytes, for example after activation of lymphocytes via signal transduction of T cell receptor (TCR) or B cell receptor (BCR). PD-1 has two known ligands, i.e. PD-L1 (such as, B7-H1, CD274) and PD-L2 (such as, B7-DC, CD273), which are members of the B7 family expressed on the cell surface. When ligating a ligand, PD-1 recruits phosphatases (such as SHP-1 and SHP-2) to its intracellular tyrosine motif, which subsequently dephosphorylates effector molecules activated via signal transduction of TCR or BCR. Thus, PD-1 is capable of transducing inhibitory signals into T cells and B cells only when linked with TCR or BCR at same time.

An antibody specifically recognizing PD-1 (i.e. monoclonal antibody against PD-1) such as IgG-like antibody is generally used in therapy, however it is still to be improved because the natural IgG-like antibody exhibits severe deficiency of low persistence and short serum half-life in the blood circulation which directly affects the efficacy of treatment, thus resulting in a side effect in a patient, and increasing the frequency and dosage of drug administration thereby further increasing treatment cost. Thus, in order to prolong the serum half-life of IgG-like antibody (especially the natural IgG-like antibody) and increase the binding affinity of the IgG-like antibody to FcRn, it is of great importance to develop a new IgG-like antibody capable of increasing the binding affinity to FcRn as well as prolonging the serum half-life.

SUMMARY

Embodiments of the present disclosure aim at solving at least one of the problems existing in the related art to at least some extent. For this purpose, an object of the present disclosure is to provide a new monoclonal antibody against programmed death-1 (PD-1) which exhibits increased binding affinity to FcRn and prolonged serum half-life. It should be noted that the present disclosure is accomplished by present inventors according to the following discoveries and work.

The IgG antibody can be hydrolyzed with papain by cleaving the disulfide bond at the N-terminus of a hinge region of the IgG antibody, thus obtaining three fragments, i.e. two identical fragments of antigen binding (i.e. Fab) and a fragment crystallizable (i.e. Fc). The crystallizable fragment Fc of antibody interacts with a variety of Fc receptors and ligands, thereby conferring important effector functions to the antibody, including initiation of complement-dependent cytotoxicity (CDC), phagocytosis and antibody-dependent cell-mediated cytotoxicity (ADCC), and transportation of antibody through cellular barrier via transcytosis. In addition, the Fc fragment is important for maintaining the serum half-life of IgG-like antibody.

Neonatal Fc receptor (FcRn) is a receptor responsible for active transportation of immunoglobulin G (IgG) by epithelial cells, which is a heterodimer consisting of an alpha chain subunit and a beta chain subunit which are linked with a non-covalent bond. The Fc fragment of IgG antibody includes two identical polypeptide chains, each of them binding to a single FcRn molecule through its individual FcRn binding site. For an adult mammal, the IgG antibody binds to FcRn through the Fc fragment thereby protecting the IgG antibody from degradation, thus the Fc fragment is of critical importance in maintaining serum antibody level. The IgG antibody binding to FcRn after endocytosed by endothelial cells will circulate in blood circulation, while the IgG antibody not binding to FcRn will be degraded by lysosomes. Thus, the Fc fragment is critical for how strong the IgG antibody binds to FcRn.

Based on the above, the present inventors have attempted to prolong the serum half-life of an IgG-like antibody and increase the binding affinity of the IgG-like antibody to FcRn by changing the sequence of a heavy chain constant region of IgG-like antibody (i.e. the sequence of Fc fragment), with IgG-like antibody H2L2 specifically recognizing PD-1 as an object. That is, the present inventors aim at improving the serum half-life and the binding affinity to FcRn by mutating the amino acids in Fc fragment of IgG-like antibody H2L2. It is found in surprise by the present inventors after a series of experimental designs and researches that the binding affinity of the IgG-like antibody H2L2 to FcRn can be improved by introducing amino acid mutations to the Fc fragment of H2L2 antibody, thus increasing the serum half-life of the IgG-like antibody H2L2. In specific, the Fc fragment of the IgG-like antibody H2L2 is mutated at amino acid positions 254, 308 and 434 with amino acids which are different from those in a wild-type IgG-like antibody (which contains no amino acid mutation), thus obtaining an optimized antibody which exhibits prolonged serum half-life compared to the wild-type IgG-like antibody while the binding affinity to and recognition specificity for antigen PD-1 is maintained.

Thus, in one aspect, the present disclosure in embodiments provides a monoclonal antibody against PD-1 or antigen-binding fragment thereof. In some embodiments, the monoclonal antibody includes a neonatal Fc Receptor (FcRn)-binding site having an amino acid sequence of SEQ ID NO: 5.

(SEQ ID NO: 5)
ASTKGSVFPLAPCSRSTSESTAALGCLVKDYFPEPVTVSWNSGALTG

VHTFPAVLQSSGLYSLSSVVTVPSSSLGTKTYTCNVDHKPSNTKVDK

RVESKYGPPCPPCPAPEFLGGPSVFLFPPKPKDTLMI [T]RTPEVTCV

VVDVSQEDPEVQFNWYVDGVEVHNAKTKPREEQFNSTYRVVSVLT [P]

LHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDG

SFFLYSRLTVDKSRWQEGNVFSCSVMHEALH [A]HYTQKSLSLSLGK, in which, the amino acids boxed respectively represent the amino acids at positions 254, 308 and 434 in the FcRn-binding site of a heavy chain constant region of the monoclonal antibody against PD-1. That is, according to the embodiment, the monoclonal antibody against PD-1 of the present disclosure (i.e. IgG-like antibody) has the amino acid threonine at position 254, the amino acid proline at position 308 and the amino acid alanine at position 434 in the FcRn-binding site of the heavy chain constant region. The present inventors found surprisingly that the monoclonal antibody against PD-1 exhibits strong binding affinity to FcRn and prolonged serum half-life, as well as strong binding affinity to and good recognition specificity for antigen PD-1.

In some embodiments, the monoclonal antibody against PD-1 includes a heavy chain having the amino acid sequence of SEQ ID NO: 1, and a light chain having the amino acid sequence of SEQ ID NO: 3. Herein, the monoclonal antibody against PD-1 named H8L2, has an amino acid mutation to threonine at position 254, an amino acid mutation to proline at position 308 and an amino acid mutation to alanine at position 434 in the FcRn-binding site of the heavy chain constant region compared to a wild-type H2L2 antibody. Thus, the monoclonal antibody against PD-1 of the present disclosure (i.e. H8L2) exhibits strong binding affinity to FcRn and prolonged serum half-life compared to the wild-type H2L2 antibody, while the binding affinity to and recognition specificity for antigen PD-1 is maintained.

In another aspect, the present disclosure in embodiments provides an isolated polynucleotide. In some embodiments, the polynucleotide encodes the antibody or antigen-binding fragment thereof described above. In some embodiments, the antibody encoded by the isolated polynucleotide exhibits strong binding affinity to FcRn and prolonged serum half-life, as well as strong binding affinity to and good recognition specificity for antigen PD-1.

In some embodiments, the polynucleotide includes a nucleotide sequence of SEQ ID NO: 6 or complementary sequence thereof, wherein the nucleotide sequence of SEQ ID NO: 6 encodes the FcRn-binding site having the amino acid sequence of SEQ ID NO: 5.

(SEQ ID NO: 6)
AAGGGCGAAGCATGGTTTGCCTATTGGGGCCAGGGAACCCTGGTCAC

CGTCTCCTCAGCTTCCACCAAGGGCCCATCCGTCTTCCCCCTGGCGC

CCTGCTCCAGGAGCACCTCCGAGAGCACAGCCGCCCTGGGCTGCCTG

GTCAAGGACTACTTCCCCGAACCGGTGACGGTGTCGTGGAACTCAGG

CGCCCTGACCAGCGGCGTGCACACCTTCCCGGCTGTCCTACAGTCCT

-continued
CAGGACTCTACTCCCTCAGCAGCGTGGTGACTGTGCCCTCCAGCAGC

TTGGGCACGAAGACCTACACCTGCAACGTAGATCACAAGCCCAGCAA

CACCAAGGTGGACAAGAGAGTTGAGTCCAAATATGGTCCCCCATGCC

CACCATGCCCAGCACCTGAGTTCCTGGGGGGACCATCAGTCTTCCTG

TTCCCCCCAAAACCCAAGGACACTCTCATGATCACCCGGACCCCTGA

GGTCACGTGCGTGGTGGTGGACGTGAGCCAGGAAGACCCCGAGGTCC

AGTTCAACTGGTACGTGGATGGCGTGGAGGTGCATAATGCCAAGACA

AAGCCGCGGGAGGAGCAGTTCAACAGCACGTACCGTGTGGTCAGCGT

CCTCACCCCCCTGCACCAGGACTGGCTGAACGGCAAGGAGTACAAGT

GCAAGGTCTCCAACAAAGGCCTCCCGTCCTCCATCGAGAAAACCATC

TCCAAAGCCAAAGGGCAGCCCCGAGAGCCACAGGTGTACACCCTGCC

CCCATCCCAGGAGGAGATGACCAAGAACCAGGTCAGCCTGACCTGCC

TGGTCAAAGGCTTCTACCCCAGCGACATCGCCGTGGAGTGGGAGAGC

AATGGGCAGCCGGAGAACAACTACAAGACCACGCCTCCCGTGCTGGA

CTCCGACGGCTCCTTCTTCCTCTACAGCAGGCTAACCGTGGACAAGA

GCAGGTGGCAGGAGGGGAATGTCTTCTCATGCTCCGTGATGCATGAG

GCTCTGCACGCCCACTACACACAGAAGAGCCTCTCCCTGTCTCTGGG

TAAA

Thus, the antibody encoded by the isolated polynucleotide has threonine, proline and alanine respectively at amino acid positions 254, 308 and 434 in the FcRn binding site of the heavy chain constant region. Further, the antibody exhibits strong binding affinity to FcRn and prolonged serum half-life, as well as strong binding affinity to and good recognition specificity for antigen PD-1.

In some embodiments, the polynucleotide is of a nucleotide sequence of SEQ ID NO: 2. Thus, the antibody encoded by the isolated polynucleotide has an amino acid mutation to threonine at position 254, an amino acid mutation to proline at position 308 and an amino acid mutation to alanine at position 434 in the FcRn-binding site of the heavy chain constant region compared to the wild-type H2L2 antibody. Further, the monoclonal antibody against PD-1 of the present disclosure exhibits strong binding affinity to FcRn and prolonged serum half-life compared to the wild-type H2L2 antibody, while the binding affinity to and recognition specificity for antigen PD-1 is maintained.

In another aspect, the present disclosure in embodiments provides an expression vector. In some embodiments, the expression vector includes the polynucleotide described above.

In still another aspect, the present disclosure in embodiments provides a recombinant cell. In some embodiments, the recombinant cell includes the expression vector described above.

It is found by the present inventors that the antibody specifically recognizing PD-1 or antigen-binding fragment thereof according to some embodiments can be efficiently synthesized by culturing the recombinant cell described above. Thus, in a further aspect, the present disclosure in embodiments provides a method for preparing the antibody or antigen-binding fragment thereof described above. In some embodiments, the method includes culturing the recombinant cell described above. Regarding the antibody or antigen-binding fragment thereof specifically recognizing PD-1, the features and advantages described above are equally applicable to the method and will not be described herein.

In a still further aspect, the present disclosure in embodiments also provides use of the polynucleotide, of the expression vector or of the recombinant cell described above in the preparation of an antibody or antigen-binding fragment thereof, wherein the antibody specifically binds to PD-1. Thus, the present inventors have found that the antibody or antigen-binding fragment thereof capable of specifically binding to PD-1 can be efficiently produced by using the polynucleotide, the expression vector or the recombinant cell described above, with a prolonged serum half-life, a strong binding affinity to FcRn, as well as a strong binding affinity to and good recognition specificity for antigen PD-1. Further, the binding of PD-1 to its receptor can be effectively blocked by the prepared antibody or antigen-binding fragment thereof, which will further block the PD-1 receptor (such as SHP1/2) related signaling pathway, thereby effectively inhibiting tumor growth.

In a furthermore aspect, the present disclosure in embodiments provides use of the antibody or antigen-binding fragment thereof, of the polynucleotide, of the expression vector or of the recombinant cell described above in the preparation of a medicament for promoting the activation and proliferation of T cells, regulating the expression and secretion of cytokines or stimulating anti-tumor cells to generate a stronger immune response.

In a furthermore aspect, the present disclosure in embodiments provides a pharmaceutical composition. In some embodiments, the pharmaceutical composition includes the antibody or antigen-binding fragment thereof, the polynucleotide, the expression vector or the recombinant cell described above. Thus, the pharmaceutical composition can be useful in effectively promoting activation and proliferation of T cells, regulating the expression and secretion of cytokines or stimulating anti-tumor cells to generate a stronger immune response.

In a still further aspect, the present disclosure in embodiments provides a method for identifying a medicament capable of binding to PD-1. In some embodiments, the method includes contacting the antibody or antigen-binding fragment thereof described above with an antigen in the presence of a candidate, and determining a first binding amount of the antibody or antigen-binding fragment thereof to the antigen, wherein the antigen is PD-1 or fragment thereof; and contacting the antibody or antigen-binding fragment thereof described above with an antigen in the absence of the candidate, and determining a second binding amount of the antibody or antigen-binding fragment thereof to the antigen, wherein the antigen is PD-1 or fragment thereof, wherein the second binding amount higher than the first binding amount is an indication that the candidate has the ability of binding to PD-1. Thus, a candidate binding to PD-1 can be screened by using this method.

It should be noted, blocking both PD-1 and CTLA-4 is normally applied in combination with the standard tumor therapy (e.g., chemotherapy). For example, both a PD-1 blocking agent and a CTLA-4 blocking agent will effectively bind to the tissue under chemotherapy. It is demonstrated by clinical trials that same efficacy can be achieved by a chemotherapeutic drug with a reduced dosage when used in combination with both anti-PD-1 antibody and anti-CTLA-4 antibody. It is reported in literatures that Decarbazine (Docetaxel, an anticancer drug) or interleukin-2 (IL-2) in combination with both anti-PD-1 antibody and anti-CTLA-4 antibody is useful in treatment of melanoma. On one hand, the chemotherapeutic drug induces cell death, which in turn increases the level of antigens expressed by the tumor cells. On the other hand, the combined blockade of PD-1 and CTLA-4 enhances the synergistic effect with radiation therapy, surgery, hormone therapy and the like, each of which enlarges sources of the antigens in the body. Further, angiogenesis inhibitors can also be used in combination with both anti-PD-1 antibody and anti-CTLA-4 antibody to inhibit vascular proliferation, thereby further inhibiting tumor cell growth, which may also be resulted from the increased expression of the antigen in the body.

In a yet still aspect, the present disclosure in embodiments provides a drug combination. In some embodiments, the drug combination includes:

a) the antibody or antigen-binding fragment thereof, the polynucleotide, the expression vector or the recombinant cell described above; and b) an immune-enhancing agent different from a).

Thus, the drug combination achieves a better therapeutic effect for tumor.

In some embodiments, the immune-enhancing agent different from a) includes at least one selected from the group consisting of: an anti-cytotoxic T lymphocyte antigen 4 (CTLA-4) antibody, an anti-CD40 antibody, Budesonide and a salicylate; optionally, the salicylate includes at least one of sulfasalazine, olsalazine, balsalazide and mesalamine.

In addition, it should be noted that the term "amino acid" as used herein means any one of 20 natural amino acids or non-natural analogs thereof which may be present at a specific and defined position. The 20 natural amino acids can be abbreviated to a three-letter code or a one-letter code:

| Alanine | ala | A |
| Arginine | arg | R |
| Asparagine | asn | N |
| Aspartic acid | asp | D |
| Asparagine or Aspartic acid | asx | B |
| Cysteine | cys | C |
| Glutamic acid | glu | E |
| Glutamine | gln | Q |
| Glutamine or Glutamic acid | glx | Z |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | try | W |
| Tyrosine | tyr | Y |
| Valine | val | V |

The expression "amino acid position n", such as amino acid positions 254, 308 and 434, refers to the specific amino acid position in the amino acid sequence of a protein. For the Fc fragment of the present disclosure, the amino acid position can be numbered according to the EU index in Kabat.

The additional aspects and advantages of the present disclosure will be set forth partly in the following description, part of which will become apparent from the description or understood from the practice of the present disclosure.

BRIEF DESCRIPTION OF THE DRAWINGS

The above and/or additional aspects and advantages of the present disclosure will become apparent and readily understood from the description of examples in combination with the following figures, in which:

FIG. 9 is a graph showing individual plasma concentration after administration of H8L2 antibody in 3 mg/kg in a pharmacokinetic study of Cynomolgus monkey (*Macaca fascicularis*) according to some embodiments of the present disclosure;

FIG. 10 is a graph showing individual plasma concentration after administration of H8L2 antibody in 10 mg/kg in a pharmacokinetic study of Cynomolgus monkey (*Macaca fascicularis*) according to some embodiments of the present disclosure;

FIG. 11 is a graph showing individual plasma concentration after administration of wild-type H2L2 antibody in 10 mg/kg in a pharmacokinetic study of Cynomolgus monkey (*Macaca fascicularis*) according to some embodiments of the present disclosure;

FIG. 12 is a graph showing effective average half-life of wild-type H2L2 and H8L2 antibodies in a pharmacokinetic study of Cynomolgus monkey (*Macaca fascicularis*) according to some embodiments of the present disclosure;

DETAILED DESCRIPTION

Figure 1:
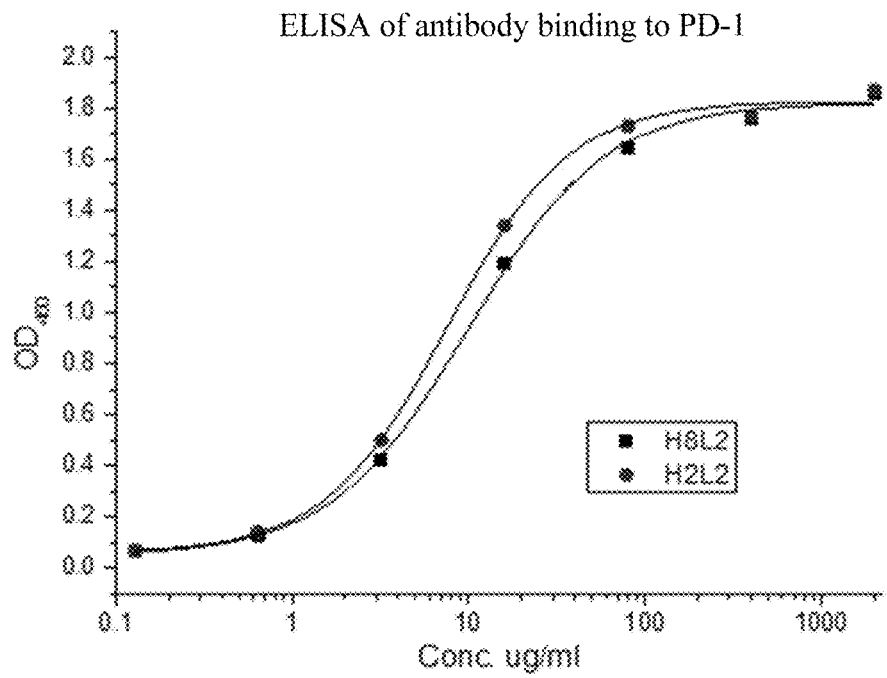
FIG. 1 is a graph showing ELISA results of H8L2 and H2L2 antibodies binding to PD-1 according to some embodiments of the present disclosure.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al. (translated by Huang P T), *Molecular Cloning: A Laboratory Manual,* 3rd Ed., Science Press) or in accordance with the product instructions. If the manufacturers of reagents or instruments are not specified, the reagents or instruments may be commercially available, for example, from Illumina Company.

Example 1 Protein Expression of H8L2 Antibody

For humanized H2L2 antibody (IgG-like antibody against PD-1), amino acids at positions 254, 308, and 434 in the FcRn-binding site of the heavy chain constant region were respectively mutated to threonine, proline and alanine, giving in a variant named as IgG-like antibody H8L2 against PD-1 (i.e. H8L2 antibody).

That is, the H8L2 antibody of interest has a threonine mutation at amino acid position 254, a proline mutation at amino acid position 308 and an alanine mutation at amino acid position 434 in the FcRn-binding site of the heavy chain constant region, with remaining amino acids unchanged, compared to the humanized H2L2 antibody.

In practice, the nucleic acid sequence encoding the humanized H8L2 antibody which is formed via Gene Synthesis was constructed into an expression vector, which was transfected into a mammalian cell 293 cell. After transfection, the humanized H8L2 antibody was expressed and secreted by the mammalian cell 293 cell. Subsequently, such the humanized H8L2 antibody obtained was purified with a protein-A affinity column, thus obtaining purified humanized H8L2 antibody, which will be used for pharmacology study after quality identification by standard SDS-PAGE and SEC-HPLC methods.

Figure 13:
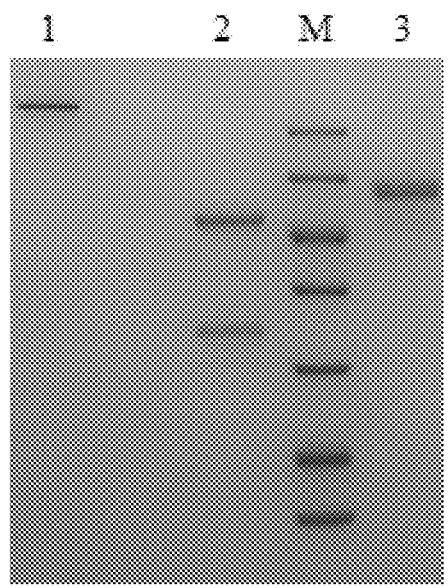
FIG. 13 is a graph showing SDS-PAGE result of H8L2 antibody according to an embodiment of the present disclosure.
Figure 14:
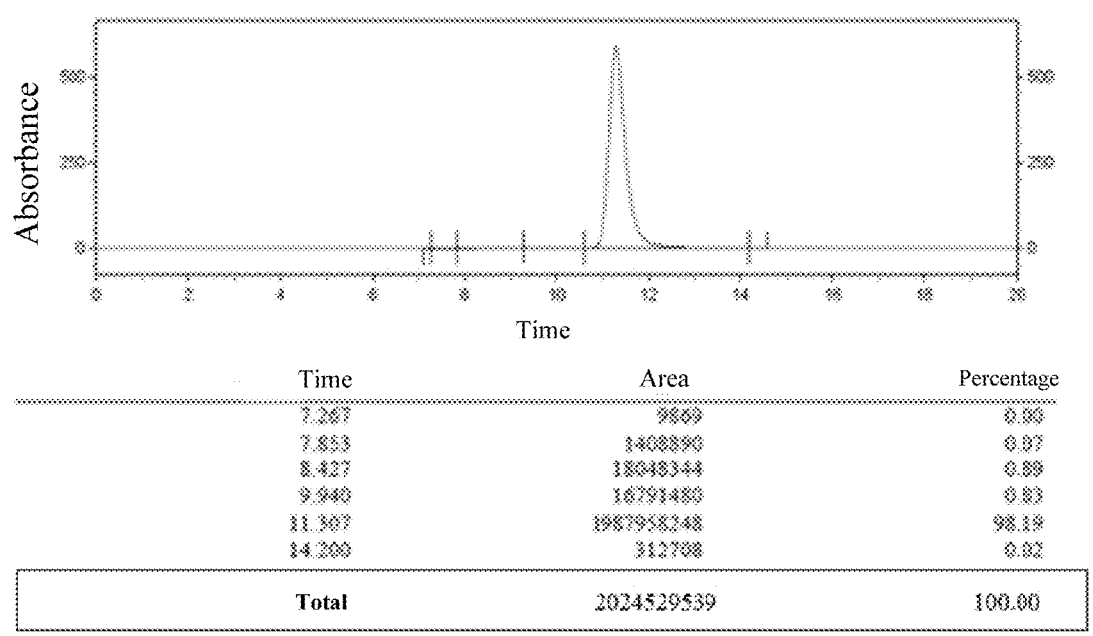
FIG. 14 is a graph showing SEC-HPLC result of H8L2 antibody according to an embodiment of the present disclosure.

Among them, results of the humanized H8L2 antibody identified by the SDS-PAGE and SEC-HPLC methods are respectively shown in FIG. 13 and FIG. 14.

FIG. 13 shows the SDS-PAGE result of H8L2 antibody, in which Lane 1 refers to a non-reduced H8L2, Lane 2 refers to a reduced H8L2, Lane 3 refers to bovine serum albumin (BSA) and Lane M refers to a DNA standard (including 14.4 KDa, 18.4 KDa, 25 KDa, 35 KDa, 45 KDa, 66.2 KDa and 116 KDa). It can be seen, candidate antibody 18A10 H8L2 is of a high overall purity.

FIG. 14 shows the SEC-HPLC result of H8L2 antibody, from which it can be seen that the candidate antibody 18A10 H8L2 is of a purity of 98.19% after confirmed by integral quantitation.

As described above, the difference between the humanized H2L2 and H8L2 antibodies only lies in the amino acids at positions 254, 308 and 434 in the FcRn-binding site of the heavy chain constant region, therefore just providing the amino acid sequence of the H8L2 antibody for reference.

Heavy chain of the humanized H8L2 antibody is of an amino acid sequence:

(SEQ ID NO: 1)
<u>EVQLVQSGGGLVQPGGSLKLSCAASGFTFSSYGMSWVRQAPGKGLDW</u>
<u>VATISGGGRDTYYPDSVKGRFTISRDNSKNNLYLQMNSLRAEDTALY</u>
<u>YCARQKGEAWFAYWGQGTLVTVSS</u>ASTKGPSVFPLAPCSRSTSESTA
ALGCLVKDYFPEPVTVSWNSGALTSGVHTFPAVLQSSGLYSLSSVVT
VPSSSLGTKTYTCNVDHKPSNTKVDKRVESKYGPPCPPCPAPEFLGG
PSVFLFPPKPKDTLMI[T]RTPEVTCVVVDVSQEDPEVQFNWYVDGVEV
HNAKTKPREEQFNSTYRVVSVLT[P]LHQDWLNGKEYKCKVSNKGLPSS
IEKTISKAKGQPREPQVYTLPPSQEEMTKNQVSLTCLVKGFYPSDIA
VEWESNGQPENNYKTTPPVLDSDGSFFLYSRLTVDKSRWQEGNVFSC
SVMHEALH[A]HYTQKSLSLSLGK, in which the heavy chain variable region of the H8L2 antibody is underlined; and the mutation sites of the H8L2 antibody (relative to H2L2 antibody) are boxed, respectively being amino acid mutations at positions 254, 308 and 434 in the FcRn-binding site of the heavy chain constant region.

Specifically, for the amino acid mutations in the FcRn-binding site of the heavy chain constant region of H8L2 antibody, the amino acid at position 254 is mutated into threonine from serine, the amino acid at position 308 is mutated into proline from valine, and the amino acid at position 434 is mutated into alanine from asparagine, compared to the humanized H2L2 antibody.

Nucleic acid sequence encoding the heavy chain of the humanized H8L2 antibody is below:

(SEQ ID NO: 2)
ATGGGATGGAGCTGTATCATCCTCTTCTTGGTAGCAACAGCTACAGG
<u>CGCGCACTCCGAGGTGCAGCTGGTGCAGTCTGGCGGCGGACTGGTGC</u>
<u>AGCCCGGCGGGTCACTGAAGCTGAGCTGCGCCGCTTCCGGCTTCACC</u>
<u>TTTAGCTCCTACGGAATGTCCTGGGTGCGACAGGCACCCGGGAAGGG</u>
<u>GCTGGACTGGGTCGCTACTATCTCAGGAGGCGGGAGAGACACCTACT</u>
<u>ATCCTGATAGCGTCAAGGGCCGGTTCACAATTAGCCGGGACAACAGC</u>
<u>AAGAACAATCTGTACCTGCAGATGAACAGCCTGAGGGCTGAGGATAC</u>
<u>TGCACTGTACTATTGTGCCCGCCAGAAGGGCGAAGCATGGTTTGCCT</u>
<u>ATTGGGGCCAGGGAACCCTGGTCACCGTCTCCTCAG</u>CTTCCACCAAG
GGCCCATCCGTCTTCCCCCTGGCGCCCTGCTCCAGGAGCACCTCCGA
GAGCACAGCCGCCCTGGGCTGCCTGGTCAAGGACTACTTCCCCGAAC
CGGTGACGGTGTCGTGGAACTCAGGCGCCCTGACCAGCGGCGTGCAC
ACCTTCCCGGCTGTCCTACAGTCCTCAGGACTCTACTCCCTCAGCAG
CGTGGTGACTGTGCCCTCCAGCAGCTTGGGCACGAAGACCTACACCT
GCAACGTAGATCACAAGCCCAGCAACACCAAGGTGGACAAGAGAGTT
GAGTCCAAATATGGTCCCCCATGCCCACCATGCCCAGCACCTGAGTT

CCTGGGGGGACCATCAGTCTTCCTGTTCCCCCCAAAACCCAAGGACA
CTCTCATGATCACCCGGACCCCTGAGGTCACGTGCGTGGTGGTGGAC
GTGAGCCAGGAAGACCCCGAGGTCCAGTTCAACTGGTACGTGGATGG
CGTGGAGGTGCATAATGCCAAGACAAAGCCGCGGGAGGAGCAGTTCA
ACAGCACGTACCGTGTGGTCAGCGTCCTCACCCCCCTGCACCAGGAC
TGGCTGAACGGCAAGGAGTACAAGTGCAAGGTCTCCAACAAAGGCCT
CCCGTCCTCCATCGAGAAAACCATCTCCAAAGCCAAAGGGCAGCCCC
GAGAGCCACAGGTGTACACCCTGCCCCCATCCCAGGAGGAGATGACC
AAGAACCAGGTCAGCCTGACCTGCCTGGTCAAAGGCTTCTACCCCAG
CGACATCGCCGTGGAGTGGGAGAGCAATGGGCAGCCGGAGAACAACT
ACAAGACCACGCCTCCCGTGCTGGACTCCGACGGCTCCTTCTTCCTC
TACAGCAGGCTAACCGTGGACAAGAGCAGGTGGCAGGAGGGGAATGT
CTTCTCATGCTCCGTGATGCATGAGGCTCTGCACGCCCACTACACAC
AGAAGAGCCTCTCCCTGTCTCTGGGTAAA, in which the nucleic acid sequence encoding the heavy chain variable region is underlined.

Light chain of the humanized H8L2 antibody is of an amino acid sequence:
<u>DIVLTQSPASLAVSPGQRATITCRASESVDNYGISFM</u>
<u>NWFQQKPGQPPKLLIYAASNKGTGVPARFSGSGSGT</u>
<u>DFTLNINPMEENDTAMYFCQQSKEVPWTFGGGTKL</u>
<u>EIKR</u>TVAAPSV FIFPPSDEQLKSGTASVVCLLNNFY-
PREAKVQWKVDNALQSGNSQESVT
EQDSKDSTYSL SSTLTLSKADYEKHKVY-
ACEVTHQGLSSPVTKSFNRGEC (SEQ ID NO: 3), in which the light chain variable region of the H8L2 antibody is underlined.

The nucleic acid encoding the light chain of the humanized H8L2 antibody is of a nucleotide sequence:

(SEQ ID NO: 4)
ATGGGATGGAGCTGTATCATCCTCTTCTTGGTAGCAACAGCTACAGG
CGTGCACTCC<u>GATATTGTGCTGACTCAGAGCCCTGCTTCCCTGGCCG</u>
<u>TGTCTCCAGGACAGCGAGCTACCATCACATGCAGAGCATCTGAGAGT</u>
<u>GTGGACAACTACGGAATTAGTTTCATGAATTGGTTTCAGCAGAAGCC</u>
<u>CGGCCAGCCCCCTAAACTGCTGATCTATGCCGCCAGCAACAAGGGCA</u>
<u>CCGGGGTGCCTGCTCGATTCTCAGGAAGCGGCTCCGGGACAGACTTT</u>
<u>ACTCTGAACATTAACCCAATGGAGGAAAATGATACAGCAATGTACTT</u>
<u>CTGCCAGCAGAGCAAGGAGGTGCCCTGGACCTTTGGCGGGGAACAA</u>
<u>AGCTGGAAATCAAACGAACTGTGGCTGCACCATCTGTCTTCATCTTC</u>
CCGCCATCTGATGAGCAGTTGAAATCTGGAACTGCCTCTGTTGTGTG
CCTGCTGAATAACTTCTATCCCAGAGAGGCCAAAGTACAGTGGAAGG
TGGATAACGCCCTCCAATCGGGTAACTCCCAGGAGAGTGTCACAGAG
CAGGACAGCAAGGACAGCACCTACAGCCTCAGCAGCACCCTGACGCT
GAGCAAAGCAGACTACGAGAAACACAAAGTCTACGCCTGCGAAGTCA
CCCATCAGGGCCTGAGCTCGCCCGTCACAAAGAGCTTCAACAGGGGA
GAGTGT, in which the nucleic acid sequence encoding the light chain variable region is underlined.

Example 2 ELISA Experiment of Recombinant Humanized H8L2 Antibody

The humanized H2L2 antibody and the humanized H8L2 antibody prepared in Example 1 were subjected to an ELISA binding experiment and a competitive ELISA experiment for comparison, as described in detail below.

2.1 ELISA Binding Experiments of 18A10 H8L2 and 18A10 H2L2 Antibodies

Specifically, the ELISA Binding Experiment was Conducted as Follows.

Step a): Antigen Coating

An ELISA plate was coated with PD-1-his antigen in a concentration of 0.25 μg/ml (100 μl per well) by incubation at 4° C. overnight.

Step b): Blocking

The ELISA plate coated with the PD-1-his antigen was blocked with 1% BSA in the PBS buffer at 37° C. for 2 hours and washed with 1×PBST buffer containing 1% Tween-20 for three times, with gently patting to dryness.

Step c): Incubation with Primary Antibody

The 18A10 H8L2 and 18A10 H2L2 antibodies were respectively diluted from 2 μg/ml in series by 1:3, with 7 gradient antibody solutions obtained. The 7 gradient antibody solutions of each of the 18A10 H8L2 and 18A10 H2L2 antibodies were respectively added into the blocked ELISA plate for incubation at 37° C. for 1 hour, with the PBS solution as a blank control.

Step d): Incubation with Secondary Antibody

After the ELISA plate was washed with the PBST buffer for three times and gently patted to dryness, goat anti-human IgG-HRP (H+L) as a secondary antibody in 1:10000 dilution (100 μl per well) was added for incubation at 37° C. for 1 hour.

Step e): Developing

After the ELISA plate was washed with the PBST buffer for three times and gently patted to dryness again, 3,3',5,5'-Tetramethylbenzidine (TMB) as a developer in 100 μl per well was added for incubation at room temperature for 5 to 10 minutes.

Step f): Termination of Developing

2M H2SO4 solution in 50 μl per well was added to terminate developing.

Step g): Reading

The absorbance of solution in each well was measured with the microplate reader at a wavelength of 450 nm.

FIG. 1 shows the results, from which the $EC_{50}$ values of H8L2 and H2L2 binding to PD-1 are respectively calculated to be 0.04 nM and 0.05 nM. As can be seen from FIG. 1, the mutation in the FcRN-binding site has no effect on the binding of antibody to PD-1.

| Series dilution of antibody | 18A10 H8L2 | | 18A10 H2L2 | |
|---|---|---|---|---|
| 2 μg/ml | 1.881 | 1.84 | 1.9 | 1.847 |
| 1:3 | 1.756 | 1.756 | 1.784 | 1.757 |
| 1:9 | 1.661 | 1.628 | 1.716 | 1.736 |
| 1:27 | 1.214 | 1.156 | 1.341 | 1.34 |
| 1:81 | 0.429 | 0.419 | 0.514 | 0.491 |
| 1:243 | 0.127 | 0.125 | 0.146 | 0.14 |
| 1:729 | 0.072 | 0.066 | 0.068 | 0.069 |
| 0 | 0.052 | 0.05 | 0.054 | 0.048 |

2.2 Competitive ELISA Experiments of 18A10 H8L2 and 18A10 H2L2 Antibodies with PDL1

Specifically, the competitive ELISA experiment was conducted as follows.

Step a): Antigen Coating

A 96-well ELISA plate was coated with PD-1-hIgGFc antigen in a concentration of 0.5 μg/ml (50 μl per well) by incubation at 4° C. overnight.

Step b): Blocking

After washed with the PBST buffer for three times and gently patted to dryness, the 96-well ELISA plate was blocked with 1% BSA in the PBS buffer at 37° C. for 2 hours and washed with the 1×PBST buffer containing 1% Tween-20 for three times.

Step c): Incubation with Primary Antibody

The 18A10 H8L2 and 18A10 H2L2 antibodies were respectively diluted from 6 μg/ml in series by 1:3, with 7 gradient antibody solutions obtained. The 7 gradient antibody solutions of each of the 18A10 H8L2 and 18A10 H2L2 antibodies (50 μl per well) were respectively added into the blocked 96-well ELISA plate for incubation at room temperature for 10 minutes, with the PBS solution as a blank control.

Step d): Incubation with Ligand 0.6 μg/ml of PDL1-mIgG2aFc solution in 50 μl per well was added for incubation at 37° C. for 1 hour.

Step e): Incubation with Secondary Antibody

After the 96-well ELISA plate was washed with the PBST buffer for three times and gently patted to dryness, goat anti-mouse IgG-HRP (H+L) as a secondary antibody in 1:5000 dilution (50 μl per well) was added for incubation at 37° C. for 1 hour.

Step f): Developing

After the 96-well ELISA plate was washed with the PBST buffer for three times and gently patted to dryness again, TMB as a developer in 50 μl per well was added for incubation at room temperature for 5 to 10 minutes.

Step g): Termination of Developing

2M H2SO4 solution in 50 μl per well was added to terminate developing.

Step h): Reading

The absorbance of solution in each well was measured with the microplate reader at a wavelength of 450 nm.

Figure 2:
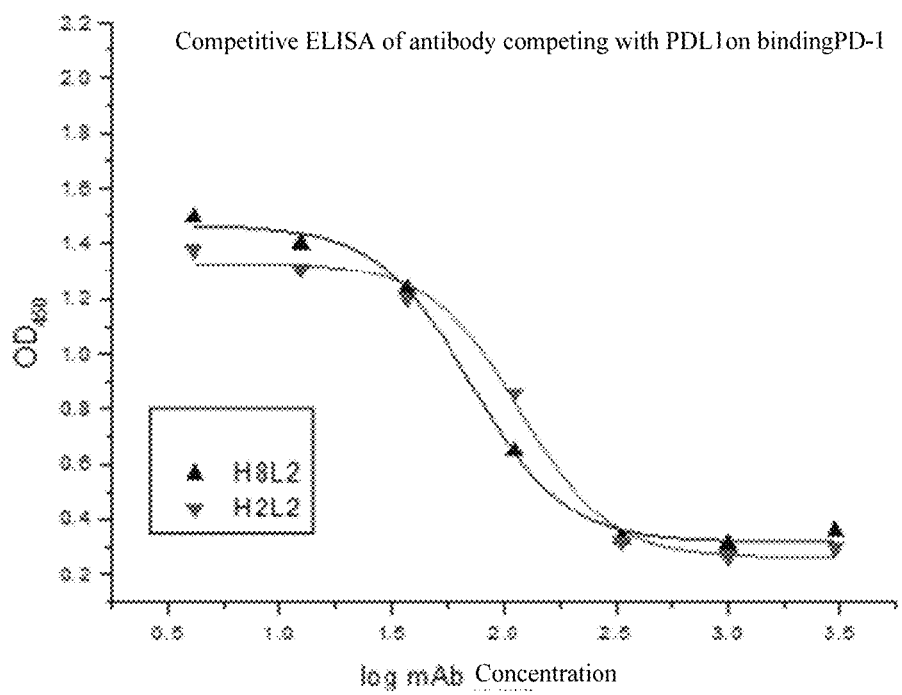
FIG. 2 is a graph showing competitive ELISA results of H8L2 and H2L2 antibodies competing with PdL1 on binding Pd-1 according to some embodiments of the present disclosure.

FIG. 2 shows the results, from which the $EC_{50}$ values of H8L2 and H2L2 antibodies competitively binding to PD-1 in the presence of PD-L1 are respectively 0.474 nM and 0.783 nM, which demonstrates the mutation in the FcRN-binding site has no effect on the competitively binding to PD-1 in the presence of PD-L1.

| Series dilution of antibody | 18A10 H8L2 | | 18A10 H2L2 | |
|---|---|---|---|---|
| 3 μg/ml | 0.367 | 0.348 | 0.301 | 0.294 |
| 1:3 | 0.329 | 0.293 | 0.26 | 0.276 |
| 1:9 | 0.325 | 0.34 | 0.335 | 0.31 |
| 1:27 | 0.658 | 0.642 | 0.828 | 0.883 |
| 1:81 | 1.275 | 1.194 | 1.191 | 1.214 |
| 1:243 | 1.454 | 1.344 | 1.276 | 1.336 |
| 1:729 | 1.489 | 1.5 | 1.385 | 1.369 |
| 0 | 2.113 | 2.067 | 2.09 | 1.417 |
| Ligand | PDL1-mIgG2aFc 0.3 μg/ml | | | |

2.3 Competitive ELISA Experiments of 18A10 H8L2 and 18A10 H2L2 Antibodies with PDL2

Specifically, the competitive ELISA experiment was conducted as follows.

Step a): Antigen Coating

A 96-well ELISA plate was coated with PD-1-hIgGFc antigen in a concentration of 1.0 μg/ml (100 μl per well) by incubation at 4° C. overnight.

Step b): Blocking

After washed with the PBST buffer for three times and gently patted to dryness, the 96-well ELISA plate was blocked with 1% BSA in the PBS buffer at 37° C. for 2 hours and washed with the 1×PBST buffer containing 1% Tween-20 for four times.

Step c): Incubation with Primary Antibody

The 18A10 H8L2 and 18A10 H2L2 antibodies were respectively diluted from 20 μg/ml in series by 1:3, with 7 gradient antibody solutions obtained. The 7 gradient antibody solutions of each of the 18A10 H8L2 and 18A10 H2L2 antibodies (50 μl per well) were respectively added into the blocked 96-well ELISA plate for incubation at room temperature for 10 minutes, with the PBS solution as a blank control.

Step d): Incubation with Ligand 1.0 μg/ml of PDL2-his tag solution in 50 μl per well was added for incubation at 37° C. for 1 hour.

Step e): Incubation with Secondary Antibody

After the 96-well ELISA plate was washed with the PBST buffer for five times and gently patted to dryness, HRP-conjugated monoclonal mouse anti-his tag as a secondary antibody in 1:750 dilution (50 μl per well) was added for incubation at 37° C. for 1 hour.

Step f): Developing

After the 96-well ELISA plate was washed with the PBST buffer for six times and gently patted to dryness again, TMB as a developer in 100 μl per well was added for incubation at room temperature for 30 minutes.

Step g): Termination of Developing

2M H2504 solution in 50 μl per well was added to terminate developing.

Step h): Reading

The absorbance of solution in each well was measured with the microplate reader at a wavelength of 450 nm.

Figures 3, 4:
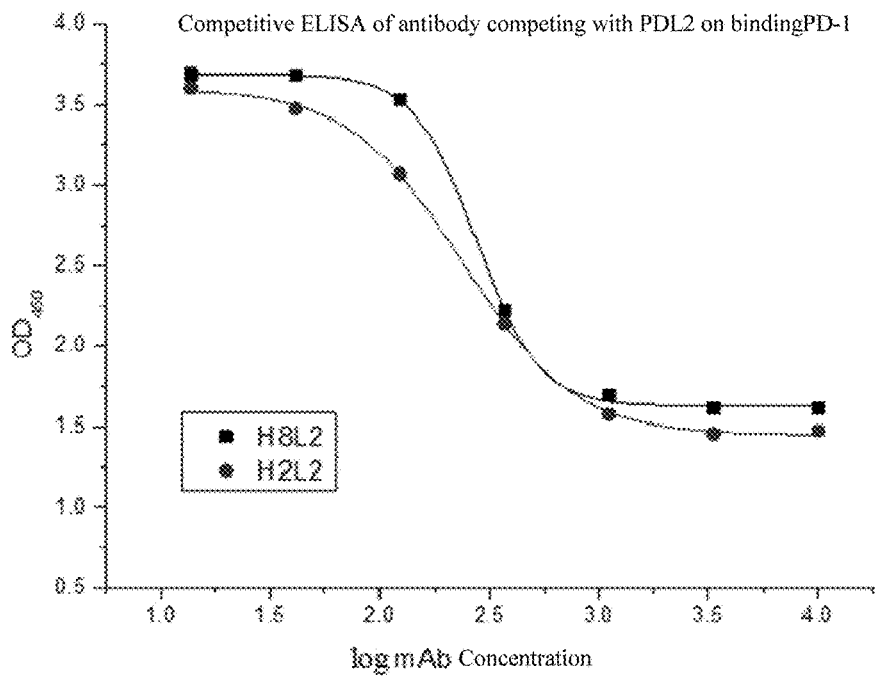
FIG. 3 is a graph showing competitive ELISA results of H8L2 and H2L2 antibodies competing with PdL2 on binding Pd-1 according to some embodiments of the present disclosure.
FIG. 4 is a graph showing the Kinetic characteristic parameters of H8L2 and H2L2 antibodies according to some embodiments of the present disclosure.

FIG. 3 shows the results, from which the $EC_{50}$ values of H8L2 and H2L2 antibodies competitively binding to PD-1 in the presence of PDL2 are respectively 1.83 nM and 1.58 nM, which demonstrates the mutation in the FcRN-binding site has no effect on the competitively binding to PD-1 in the presence of PDL2.

| Series dilution of antibody | 18A10 H8L2 | | 18A10 H2L2 | |
| --- | --- | --- | --- | --- |
| 10 μg/ml | 1.681 | 1.551 | 1.493 | 1.454 |
| 1:3 | 1.628 | 1.596 | 1.46 | 1.455 |
| 1:9 | 1.74 | 1.643 | 1.585 | 1.566 |
| 1:27 | 2.101 | 2.331 | 2.206 | 2.072 |
| 1:81 | 3.485 | 3.577 | 3.139 | 3 |
| 1:243 | 3.682 | 3.685 | 3.476 | 3.475 |
| 1:729 | 3.692 | 3.682 | 3.773 | 3.432 |
| Blank | 0.401 | 0.28 | | |
| Ligand | PDL2-his tag 0.5 μg/ml | | | |

2.4 Binding Activity of H8L2 Antibody to PD1-hFc of Cynomolgus Monkey (*Macaca fascicularis*)

In this experiment, the binding activity of H8L2 antibody to a non-human antigen (such as PD1 of Cynomolgus monkey) was detected by the ELISA method to reflect the cross-reactivity of H8L2 antibody with non-human antigen.

An ELISA plate was coated with PD1-hFc of Cynomolgus monkey (*Macaca fascicularis*) in a concentration of 0.125 μg/ml (50 μl per well) by incubation at 4° C. overnight. After washed with the PBST buffer once and gently patted to dryness, the ELISA plate was blocked with 1% BSA in the PBS buffer (300 μl per well) at 37° C. for 2 hours. The blocked ELISA plate was washed with the PBST buffer once and gently patted to dryness. The H8L2 antibody diluted to 7 nM as a starting concentration was further diluted in series by 1:3 in a plate, followed by adding into the blocked ELISA plate in 100 μl per well for incubation at 37° C. for 30 minutes in duplicate, with the PBS solution as a blank control. After the ELISA plate was washed with the PBST buffer for three times, goat anti-human IgG F(ab')2-HRP as a secondary antibody was added in 50 μl per well for incubation at 37° C. for 30 minutes. The ELISA plate was washed with the PBST buffer for four times, and TMB as a developer in 50 μl per well was added for incubation at room temperature for 5 minutes in dark. After 2M H2504 solution in 50 μl per well was added to terminate developing, the ELISA plate was measured with the microplate reader at a wavelength of 450 nm to obtain the absorbance of solution in each well, with data analysis and processing by SoftMax Pro 6.2.1 software.

The detection results of the binding activity of H8L2 antibody to PD1-hFc of Cynomolgus monkey (*Macaca fascicularis*) at a wavelength of 450 nm are shown in the following table.

| Series dilution of antibody | H8L2 | |
| --- | --- | --- |
| 1 μg/ml | 2.446 | 2.339 |
| 1:3 | 2.355 | 2.390 |
| 1:9 | 1.928 | 2.152 |
| 1:27 | 1.369 | 1.455 |
| 1:81 | 0.637 | 0.648 |
| 1:243 | 0.343 | 0.288 |
| 1:729 | 0.159 | 0.167 |
| 0 | 0.087 | 0.092 |
| $EC_{50}$ (nM) | | 0.219 |

The results at a wavelength of 450 nm in the table show that $EC_{50}$ value of H8L2 antibody binding to PD1-hFc of Cynomolgus monkey (*Macaca fascicularis*) is 0.219 nM.

2.5 Binding Activity of H8L2 Antibody to PD1 of Rat (ELISA Method)

In this experiment, the binding activity of H8L2 antibody to a non-human antigen (such as PD1 of rat) was detected by the ELISA method to reflect the cross-reactivity of H8L2 antibody with non-human antigen.

An ELISA plate was coated with PD1 of rat in a concentration of 1 μg/ml (50 μl per well) by incubation at 4° C. overnight. After washed with the PBST buffer once and gently patted to dryness, the ELISA plate was blocked with 1% BSA in the PBS buffer (300 μl per well) at 37° C. for 2 hours. The blocked ELISA plate was washed with the PBST buffer for three times and gently patted to dryness. The H8L2 antibody diluted to 7 nM as a starting concentration was further diluted in series by 1:3 in a plate, followed by adding into the blocked ELISA plate in 100 μl per well for incubation at 37° C. for 30 minutes in duplicate, with the PBS solution as a blank control. After the ELISA plate was washed with the PBST buffer for three times, goat anti-human IgG-HRP as a secondary antibody was added in 50 μl per well for incubation at 37° C. for 30 minutes. The ELISA plate was washed with the PBST buffer for four times, and TMB as a developer in 50 μl per well was added for incubation at room temperature for 5 minutes in dark. After 2M H2504 solution in 50 μl per well was added to terminate developing, the ELISA plate was measured with the microplate reader at a wavelength of 450 nm to obtain the absorbance of solution in each well, with data analysis and processing by SoftMax Pro 6.2.1 software.

The detection results of the binding activity of H8L2 antibody to PD1 of rat at a wavelength of 450 nm are shown in the following table.

| Series dilution of antibody | H8L2 | |
|---|---|---|
| 7 nM | 0.098 | 0.116 |
| 1:3 | 0.061 | 0.063 |
| 1:9 | 0.052 | 0.051 |
| 1:27 | 0.047 | 0.047 |
| 1:81 | 0.044 | 0.044 |
| 1:243 | 0.044 | 0.043 |
| 1:729 | 0.044 | 0.043 |
| 0 | 0.044 | 0.043 |
| $EC_{50}$ (nM) | 3.69E+06 | |

The results at a wavelength of 450 nm in the table show that nearly no binding activity between H8L2 antibody and PD1 of rat.

Example 3 Determination of Kinetic Characteristic Parameters of H8L2 and H2L2 Antibodies with Fortebio Molecular Interaction Instrument The kinetic characteristic parameters of H8L2 antibody prepared in Example 1 and H2L2 antibody were determined using the Fortebio molecular interaction instrument for comparison, which are described in detail below.

The biotin-labeled PD-1 antigen was immobilized on the surface of the SA sensor. After equilibration with the PBST buffer, the H8L2 antibody, diluted in series by 1:3 with PBST (200 nM, 66.67 nM, 22.22 nM, 7.41 nM, 2.47 nM, 0.82 nM, 0.27 nM and 0 nM respectively), was applied to the SA sensor for binding to the biotin-labeled PD-1 antigen, after which PBST was applied to the SA sensor for disassociation. Assay for H2L2 antibody is the same as H8L2 antibody. Results of kinetic characteristic parameters of the H8L2 and H2L2 antibodies are shown in FIG. 4, from which it can be seen the mutation in the FcRN-binding site has no effect on the kinetic characteristic parameters of antibody.

Example 4 Detection of Direct and Competitive Binding Activity of H8L2 Antibody with FACS Method The direct and competitive binding activity of H8L2 antibody prepared in Example 1 was detected by using the FACS method, which is described in detail below.

4.1 Detection of Binding Activity of H8L2 Antibody to PD1 with FACS Method

In this experiment, the binding activity of H8L2 antibody to PD1 on the surface of cell membrane was detected by the FACS method, with a 293T cell line stably transfected with PD1 as an experimental cell.

Specifically, the binding experiment was conducted as follows.

Step a) The 293T cell line stably transfected with PD1 was digested and counted to obtain a cell suspension in a final concentration of $10^6$ cells/ml.

Step b) 100 μl of the cell suspension was added into a 1.5 ml EP tube for each group, with $10^5$ cells per group.

Step c) The H8L2 antibody (in concentrations of 0.01 nM, 0.10 nM, 1.00 nM, 2.50 nM, 5.00 nM, 10.00 nM, 20.00 nM and 50.00 nM) were respectively added into individual groups and incubated on ice for 1 hour.

Step d) Each group was centrifuged, followed by washing with the PBS buffer once.

Step e) FITC Goat Anti-human IgG as a secondary antibody was added into each group and incubated on ice in dark for 1 hour.

Step f) Each group was centrifuged at 4000 r/min at a low temperature for 5 minutes, followed by washing with the PBS buffer once and adding 200 μl PBS for suspending, thus obtaining a suspension for on-line detection.

Figure 15:
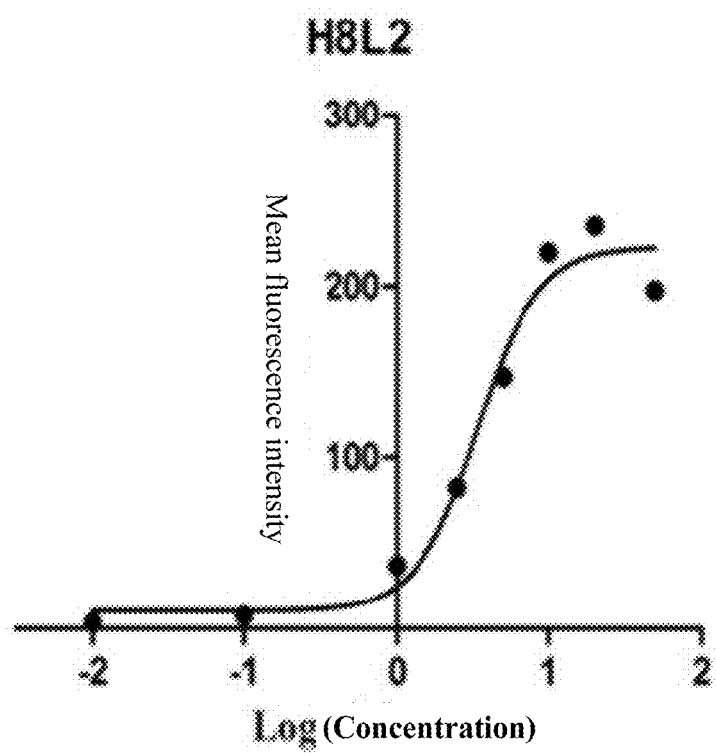
FIG. 15 is a graph showing binding activity of H8L2 antibody to PD-1 detected with the FACS method according to an embodiment of the present disclosure.

FIG. 15 and the following table show the results of binding activity of H8L2 antibody to PD1 on the surface of cell membrane detected with the FACS method.

| | Average flourescence intensity | | | | | | | | |
|---|---|---|---|---|---|---|---|---|---|
| Concentration/nM | 0.01 | 0.10 | 1.00 | 2.50 | 5.00 | 10.00 | 20.00 | 50.00 | $EC_{50}$ (nM) |
| H8L2 | 3.50 | 7.57 | 36.59 | 82.64 | 147.23 | 219.65 | 235.05 | 197.69 | 3.40 |

FIG. 15 and the table show the $EC_{50}$ value of H8L2 antibody binding to PD-1 is 3.40 nM.

4.2 Detection of Binding Activity of H8L2 Antibody to PD1 in the Presence of PDL1 with FACS Method In this experiment, the binding activity of PDL1 (i.e. a competitive protein) to PD1 on the surface of cell membrane was detected with the FACS method to reflect the binding activity of H8L2 antibody to PD1 in the presence of PDL1, with a 293T cell line stably transfected with PD1 as an experimental cell.

Specifically, the binding experiment was conducted as follows.

Step a) The 293T cell line stably transfected with PD1 was digested and counted to obtain a cell suspension in a final concentration of $10^6$ cells/ml.

Step b) 100 μl of the cell suspension was added into a 1.5 ml EP tube for each group, with $10^5$ cells per group.

Step c) The H8L2 antibody (in concentrations of 0.10 nM, 1.00 nM, 2.50 nM, 5.00 nM, 10.00 nM, 20.00 nM, 50.00 nM and 100.00 nM) were respectively added into individual groups and incubated on ice for 0.5 hours.

Step d) The ligand PDL1-mFc was added into each group with a final concentration of 20 nM, followed by incubating for another 0.5 hours.

Step e) Each group was centrifuged and washed with the PBS buffer once.

Step f) FITC Goat Anti-human IgG/IgM as a secondary antibody was added into each group and incubated on ice in dark for 1 hour.

Step g) Each group was centrifuged at 4000 r/min at a low temperature for 5 minutes, followed by washing with the PBS buffer once and adding 200 μl PBS for suspending, thus obtaining a suspension for on-line detection.

Figure 16:
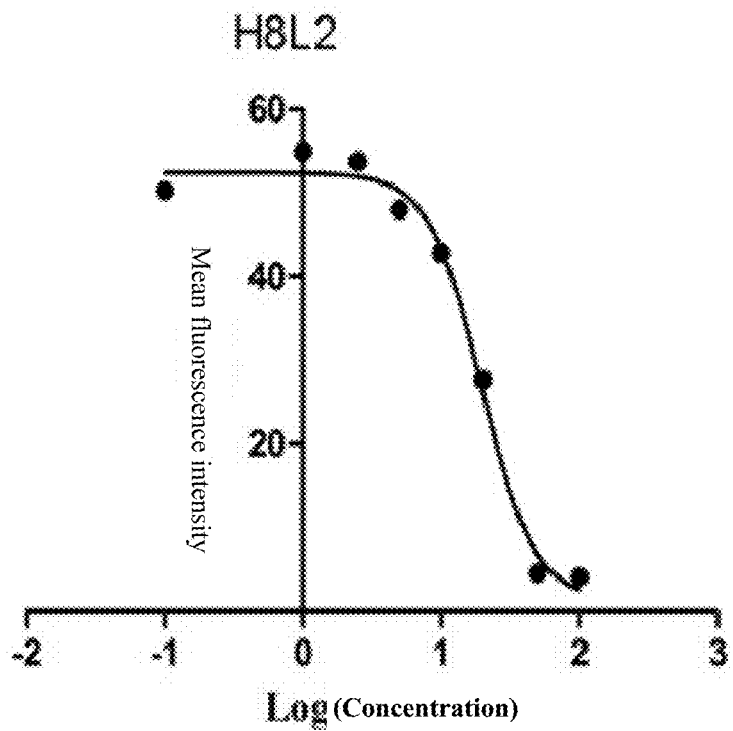
FIG. 16 is a graph showing binding activity of H8L2 antibody to PD-1 in the presence of PD-L1 detected with the FACS method according to an embodiment of the present disclosure.

FIG. 16 and the following table show the results of binding activity of H8L2 antibody to PD1 on the surface of cell membrane in the presence of PDL1 detected with the FACS method.

| | Average flourescence intensity | | | | | | | |
|---|---|---|---|---|---|---|---|---|
| Concentration/nM | 0.10 | 1.00 | 2.50 | 5.00 | 10.00 | 20.00 | 50.00 | 100.00 | $EC_{50}$ (nM) |
| H8L2 | 50.26 | 54.90 | 53.77 | 48.00 | 42.85 | 27.70 | 4.56 | 4.14 | 19.65 |

FIG. 16 and the table show the $EC_{50}$ value of 18A10 H8L2 antibody binding to PD-1 in the presence of PDL1 is 19.65 nM.

Example 5 Assay of Biological Activity of Antibody Against PD1 Under Mixed Lymphatic Reaction T lymphocytes were assayed for IL-2 and IFN gamma secretion under stimulation of H8L2 antibody prepared in Example 1 and H2L2 antibody by the mixed lymphocyte reaction (MLR) for comparison, which is described in detail below.

For MLR, T cells (TC) and dendritic cells (DC) from different human sources were mixed, such that the T cells secrete IL-2 and IFN gamma under antigen presenting function of the DC cells. Specifically, monocytes in the blood differentiate into immature DC cells under the induction of cytokines GM-CSF and IL-4, after which the immature DC cells were induced to maturation via stimulation of tumor necrosis factor alpha (TNFα). Subsequently, the matured DC cells and allogeneic TC cells were mixed and cultured for 5 days, thereafter the secreted IL-2 and IFN gamma in cell supernatant were determined. In this example, the TC cells ($1 \times 10^5$ per well) and the matured DC cells ($1 \times 10^4$ per well) were mixed in a 96 well plate, and then cultured in the presence of individual antibodies in eight gradient concentrations (i.e. from 10 μM to 0.09765625 nM) for 5 days, after which the amount of IL-2 in cell supernatant was detected with an IL-2 assay kit. Similarly, the TC cells ($1 \times 10^5$ per well) and the matured DC cells ($1 \times 10^4$ per well) were mixed in a 96 well plate, and then cultured in the presence of individual antibodies in five gradient concentrations (i.e. from 300 nM to 0.1 nM) for 5 days, after which the amount of IFN gamma in the cell supernatant was detected with an IFN gamma assay kit.

Figure 5:
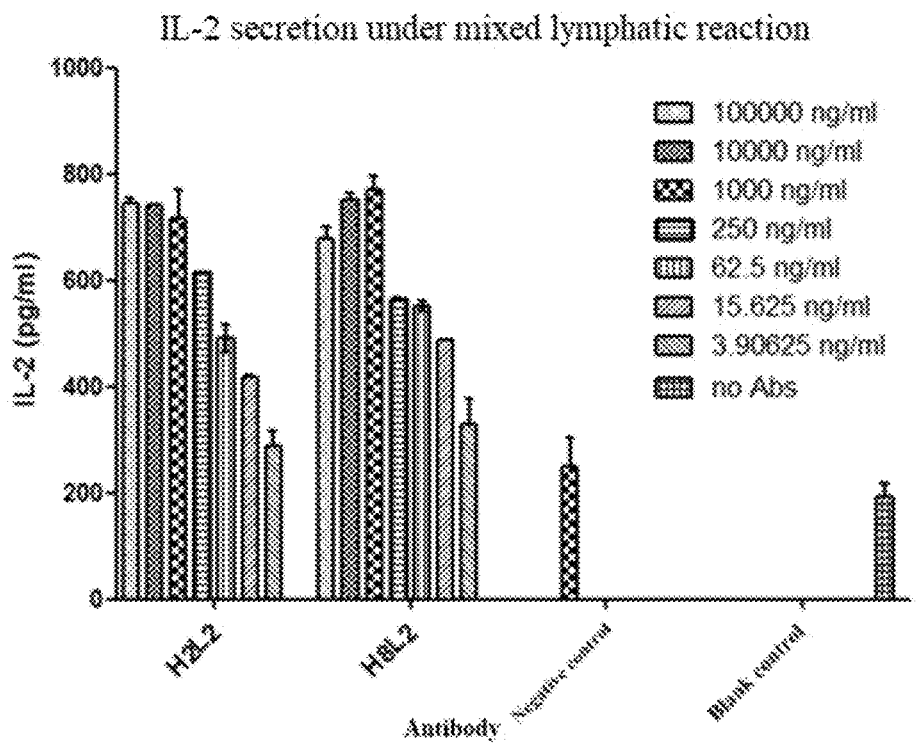
FIG. 5 is a graph showing content of IL-2 secreted by T cells under stimulation of H8L2 and H2L2 antibodies via blocking the activation of PD-1 protein according to some embodiments of the present disclosure.

FIG. 5 shows the content of IL-2 secreted by T cells under the stimulation of the H8L2 and H2L2 antibodies respectively, from which it can be seen that the H8L2 and H2L2 antibodies are capable of stimulating T cells to secrete IL-2 in an effective manner, which demonstrates that the mutation in the FcRN-binding site has no effect on the IL-2 secretion by T cells under the stimulation of antibody.

Figure 6:
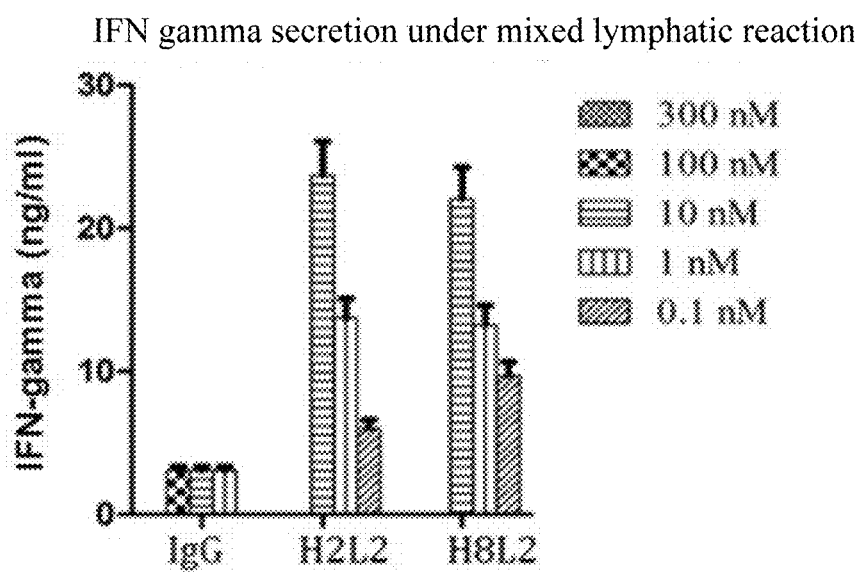
FIG. 6 is a graph showing content of IFN gamma secreted by T cells under stimulation of H8L2 and H2L2 antibodies via blocking the activation of PD-1 protein according to some embodiments of the present disclosure.

FIG. 6 shows the content of IFN gamma secreted by T cells under the stimulation of the H8L2 and H2L2 antibodies respectively, from which it can be seen that the H8L2 and H2L2 antibodies are capable of stimulating T cells to secrete IFN gamma in an effective manner, which demonstrates that the mutation in the FcRN-binding site has no effect on the IFN gamma secretion by T cells under the stimulation of antibody. The "IgG" in FIG. 6 is an isotype antibody as a control.

Example 6 Serum Concentration Study of Cynomolgus Monkey (*Macaca fascicularis*)

Serum concentrations of H8L2 antibody prepared in Example 1 and H2L2 antibody in Cynomolgus monkey (*Macaca fascicularis*) were respectively detected for comparison, which is described in detail below.

Figures 7, 8:
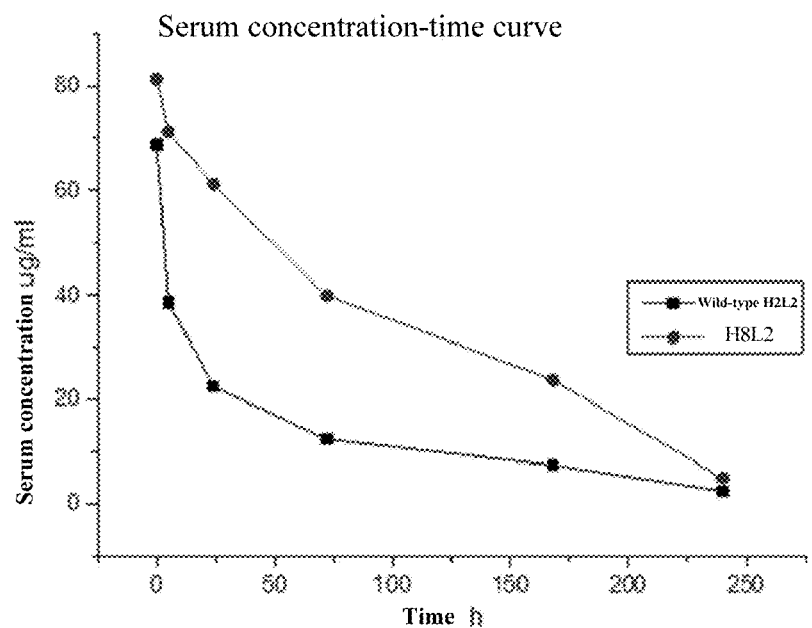
FIG. 7 is a graph showing concentration-time curves of H8L2 and H2L2 antibodies measured by ELISA in a serum concentration study of Cynomolgus monkey (*Macaca fascicularis*) according to some embodiments of the present disclosure.
FIG. 8 is a graph showing individual plasma concentration after administration of H8L2 antibody in 1 mg/kg in a pharmacokinetic study of Cynomolgus monkey (*Macaca fascicularis*) according to some embodiments of the present disclosure.

Four Cynomolgus monkeys (*Macaca fascicularis*) were randomly divided into 2 groups as their body weights, respectively named as H8L2 group and H2L2 group, with 2 animals per group. Each group was administered with its individual antibody in a dosage of 1 mg/kg by intravenous injection, with whole blood sampled before administration and after administration 5 minutes, 5 hours, 24 hours, 72 hours, 168 hours and 240 hours respectively. Blood serum was separated from the whole blood and the contents of H8L2 and H2L2 antibodies were respectively measured by the ELISA method, which can be seen in FIG. 7 and the table below.

| | Serum concentration (ug/ml) | | | | | |
|---|---|---|---|---|---|---|
| Time (h) | H2L2 | H2L2 | Mean | H8L2 | H8L2 | Mean |
| 0 | 0 | 0 | 0 | 0 | 0 | 0 |
| 0.015 (Tmax) | 62.5 | 75 | 68.75 | 95 | 67.5 | 81.25 |
| 5 | 32.5 | 45 | 38.75 | 90 | 52.5 | 71.25 |
| 24 | 22.5 | 22.5 | 22.5 | 80 | 42.5 | 61.25 |
| 72 | 15 | 10 | 12.5 | 50 | 30 | 40 |
| 168 | 10 | 5 | 7.5 | 27.5 | 20 | 23.75 |
| 240 | 5 | 0 | 2.5 | 0 | 10 | 5 |

Example 7 Pharmacokinetic Study of Cynomolgus Monkey (*Macaca fascicularis*)

Pharmacokinetics of H8L2 antibody prepared in Example 1 and H2L2 antibody in Cynomolgus monkey (*Macaca fascicularis*) was studied for comparison, which is described in detail below.

24 Cynomolgus monkeys (*Macaca fascicularis*) were randomly divided into 4 groups as their body weights, respectively named as a H2L2 group (10 mg/kg) and three H8L2 groups in different dosages (that is low: 1 mg/kg, medium: 3 mg/kg and high: 10 mg/kg), with 6 animals per group (male and female half for each group). Each group was administered with its individual antibody by intravenous injection, with whole blood sampled before administration and after administration 5 minutes, 30 minutes, 1 hour, 2 hours, 4 hours, 8 hours, 24 hours, 48 hours, 144 hours and 216 hours respectively. Blood serum was separated from the whole blood and the contents of H8L2 and H2L2 antibodies were respectively measured by the ELISA method, with relevant pharmacokinetic parameters calculated by PhoenixWinNonlin (Pharsight) 6.4.

Before single administration, the serum concentration of H2L2 and H8L2 antibodies in all cynomolgus monkey individuals is below the lower limit of quantitation. After the administration, the serum concentration of H8L2 antibody in the cynomolgus monkeys of the three H8L2 groups increases as the administration dosage, in which the effective average half-life of the low dosage group (i.e. 1 mg/kg), the medium dosage group (i.e. 3 mg/kg) and the high dosage group (i.e. 10 mg/kg) is respectively 215.72 hours (refer to FIG. 8), 288.78 hours (refer to FIG. 9) and 268.92 hours (refer to FIG. 10). Further, the effective average half-life of the wild-type H2L2 group (in a dosage of 10 mg/kg) is 224 hours (refer to FIG. 11). It can be seen, the H8L2 group exhibits longer effective average half-life than the wild-type H2L2 group under a same dosage of 10 mg/kg (refer to FIG. 12).

Example 8 Anti-Tumor Effect of H8L2 Antibody in Subcutaneously Implanted Tumor MiXeno Model of Human Non-Small Cell Lung Cancer HCC827 Cell Line Anti-tumor effect of H8L2 antibody prepared in Example 1 was investigated by using a subcutaneously implanted tumor MiXeno model established with human non-small cell lung cancer HCC827 cell line in NSG mice, which is described in detail below.

NSG mice, featured by non-obese diabetes (NOD), Prkd-$c_{scid}$ and IL2rg$_{null}$ deletion or mutation, have highest immune deficiency and thus become a most suitable tool for human-derived cell transplantation, without rejection to human-derived cells and tissues. Based on the above, the present inventors evaluated anti-tumor effect of H8L2 antibody in vivo by means of a graft-versus-host disease (GVHD) model established by adoptive transplantation of human peripheral blood mononuclear cells (PBMC) into the NSG mouse. Besides, the present inventors have established the subcutaneously implanted tumor model (i.e. MiXeno model) by using the NSG mouse, and further discovered anti-tumor effect of H8L2 antibody on the subcutaneously implanted tumor MiXeno model of human non-small cell lung cancer HCC827 cell line.

Specifically, HCC827 cells were inoculated into the right side of the back of each 40 NCG mouse (32 experimental mice plus 8 mice for a spare) in a dosage of $5 \times 10^6$ cells per mouse by subcutaneous injection on day 0 (Day 0). On day 6 post inoculation (Day 6), 32 NCG mice with a tumor size up to 66 mm$^3$ were divided into 4 groups with 8 mice per group, and each mouse was subjected to tail-intravenous transplantation of 0.1 ml PBMC (suspended in the PBS buffer). For the four groups (i.e. 32 mice), H8L2 5 mg/kg treatment group (Group 1), H8L2 10 mg/kg treatment group (Group 2), Opdivo 5 mg/kg treatment group (Group 3) as a positive control, and isotype antibody (Human IgG4) 5 mg/kg group (Group 4) as a control were administrated intravenously via the tail vein at day 6, day 9, day 13, day 16, day 19 and day 22 post inoculation respectively, with a total of 6 administrations as shown in Table 1. The efficacy was evaluated according to the relative tumor growth inhibition value (TGI$_{RTV}$), and the safety was evaluated according to the body weight change and death of mice.

TABLE 1

Experimental design for anti-tumor effect of H8L2 antibody on the MiXeno model of human non-small cell lung cancer HCC827 cell line

| Groups | n | (Day 0) Subcutaneous implantation | PBMC | Treatment | Dosage concentration (mg/kg) | Administration mode | Dosage volume | Administration time |
|---|---|---|---|---|---|---|---|---|
| 1 | 8 | $5 \times 10^6$/100 μL | tumor size of 66 mm$^3$; intravenous injection of 0.1 ml PBMC suspension per mouse on day 6 post inoculation of tumor cell | Anti-Hel-hIgG4 | 5 | intravenous (i.v.) | 10 μl/g | on day 6, day 9, day 13, day16, day 19 and day 22 post inoculation respectively |
| 2 | 8 | | | Opdivo | 5 | intravenous (i.v.) | 10 μl/g | |
| 3 | 8 | | | H8L2 | 5 | intravenous (i.v.) | 10 μl/g | |
| 4 | 8 | | | H8L2 | 10 | intravenous (i.v.) | 10 μl/g | |

Note:
Dosage volume is 10 μl/g;
n represents the number of mice;
Day 0 represents the day when tumor cells are inoculated;
i.v. represents intravenous administration via the tail vein With respect to the isotype antibody (Human IgG4) 5 mg/kg group as a control, the H8L2 10 mg/kg treatment group exhibits a significant inhibition of tumor growth on day 9 and 13 post inoculation of tumor cell, with the relative tumor growth inhibition value ($TGI_{RTV}$) of 30% (p=0.007) and 30% (p=0.039) respectively; the H8L2 5 mg/kg treatment group also shows a significant inhibition of tumor growth on day 9 and 13 post inoculation of tumor cell, with the relative tumor growth inhibition value ($TGI_{RTV}$) of 18% (p=0.049) and 25% (p=0.041) respectively; while the Opdivo 5 mg/kg treatment group does not display a more significant inhibition of tumor growth on day 9 and 13 post inoculation of tumor cell, with the relative tumor growth inhibition value ($TGI_{RTV}$) of 17% (p=0.084) and 23% (p=0.073) respectively, refer to Table 2. The results demonstrate that the H8L2 antibody is capable of significantly inhibiting the tumor growth of the tumor MiXeno model of human non-small cell lung cancer HCC827 cell line, with even better efficacy than the Opdivo group which is used as a positive control. Further, the H8L2 5 mg/kg treatment group and the H8L2 10 mg/kg treatment group do not develop drug-related toxicity (such as severe weight loss or death) similar with the Opdivo 5 mg/kg treatment group within 16 days from the first administration (i.e. Day 6 to Day 22 post inoculation), indicating well tolerance for the treatment of H8L2 antibody.

TABLE 2

Anti-tumor effect assay on the tumor MiXeno model of human non-small cell lung cancer HCC827 cell line

| Treatment groups | Day | Tumor size (mm³) (Mean ± SEM) | Relative tumor size (Mean ± SEM) | $TGI_{RTV}$ (%) | P value[1] |
|---|---|---|---|---|---|
| G1 Human IgG4 5 mg/kg | 9 | 88 ± 8 | 1.33 ± 0.08 | — | — |
| | 13 | 116 ± 12 | 1.76 ± 0.15 | — | — |
| | 16 | 132 ± 15 | 2.00 ± 0.17 | — | — |
| G2 Opclivo 5 mg/kg | 9 | 74 ± 8 | 1.11 ± 0.09 | 17 | 0.084 |
| | 13 | 91 ± 14 | 1.35 ± 0.15 | 23 | 0.073 |
| | 16 | 109 ± 11 | 1.64 ± 0.12 | 18 | 0.106 |
| G3 H8L2 5 mg/kg | 9 | 72 ± 6 | 1.09 ± 0.07 | 18 | 0.049 |
| | 13 | 87 ± 10 | 1.32 ± 0.12 | 25 | 0.041 |
| | 16 | 103 ± 12 | 1.57 ± 0.17 | 21 | 0.097 |
| G4 H8L2 10 mg/kg | 9 | 62 ± 8 | 0.93 ± 0.09 | 30 | 0.007 |
| | 13 | 82 ± 14 | 1.22 ± 0.18 | 30 | 0.039 |
| | 16 | 110 ± 24 | 1.63 ± 0.33 | 18 | 0.340 |

Note:
P value[1] is obtained by comparing with the isotype antibody (Human IgG4) 5 mg/kg group The H8L2 antibody (i.e. monoclonal antibody against PD-1) shows significant inhibition of tumor growth on the tumor MiXeno model of human non-small cell lung cancer HCC827 cell line when injected at the administration dosage of 10 mg/kg and 5 mg/kg respectively, where the H8L2 antibody at the administration dosage of 10 mg/kg exhibits even more significant inhibition of tumor growth and displays better efficacy over the Opdivo 5 mg/kg treatment group as the positive control, with well tolerance for the tumor-bearing mice under the dosage of both 10 mg/kg and 5 mg/kg.

Example 9 Anti-Tumor Effect of H8L2 Antibody in HuGEMM Model of MC38 Murine Colorectal Cancer Cell Line The efficacy of H8L2 antibody prepared in Example 1 for treatment of colorectal cancer was pre-clinically validated in the PD-1 HuGEMM MC38-bearing mouse, which is described in detail below.

MC38 cell line is a murine colorectal cancer cell line derived from C57BL/6 mouse. The PD-1 HuGEMM model is a modeled mouse which is genetically engineered by replacing some fragments of murine PD-1 protein that interacts with PD-L1 protein molecule in the C57BL/6 mouse with corresponding human-derived protein.

MC38 cells were inoculated into the right side of each subject mice in a dosage of $1 \times 10^6$ cells per mouse by subcutaneous injection. The mice with a tumor size up to 134 mm³ were randomly divided into 4 groups as the tumor size, with 8 mice per group and 4 mice per cage, named as Group 1 to Group 4, that is H8L2 5 mg/kg treatment group, H8L2 10 mg/kg treatment group, Keytruda 10 mg/kg treatment group as a positive control, and isotype antibody (Human IgG4) 5 mg/kg group as a control respectively. The corresponding antibody for each group was administrated intravenously via the tail vein of mice, with a total of 6 administrations, refer to Table 3.

TABLE 3

Experimental design for anti-tumor effect assay

| Groups | Number | Treatment | Dosage (mg/kg) | Administration mode | Dosage regimen |
|---|---|---|---|---|---|
| 1 | 8 | Isotype control | 10 | i.v. | BIW × 3 |
| 2 | 8 | Keytruda | 10 | i.v. | BIW × 3 |
| 3 | 8 | H8L2 | 5 | i.v. | BIW × 3 |
| 4 | 8 | H8L2 | 10 | i.v. | BIW × 3 |

On day 13 post grouping, the mice in the Group 1 have the average tumor size up to 1933.67 mm³, and the Group 2 (Keytruda 10 mg/kg treatment group, in a high dosage), the Group 3 (H8L2 5 mg/kg treatment group, in a low dosage) and the Group 4 (H8L2 10 mg/kg treatment group, in a high dosage) each have a tumor growth inhibition (TGI) (%) of 85%, 93% and 90% respectively, refer to Table 4; and the four groups respectively have a percentage weight change of 8.72%, 0.94%, −2.07% and 1.68%. Each of mice has no significant unexpected weight loss or death. The Groups 2 to 4 show statistically significant difference in inhibition effect compared to the group 1, each with P<0.05.

TABLE 4

Anti-tumor effect of H8L2 antibody in PD-1 HuGEMM MC38-bearing mice

| Groups | Treatment | Tumor size on Day 0[a] (mm³) | Tumor size on Day 13[a] (mm³) | TGI (%) | T-C (day) | P value[b] |
|---|---|---|---|---|---|---|
| 1 | Isotype control 10 mg/kg | 132.86 ± 14.78 | 1933.67 ± 454.6 | — | — | — |
| 2 | Keytruda 10 mg/kg | 135.35 ± 20.19 | 275.71 ± 160.18 | 85 | 10 | <0.05 |

TABLE 4-continued

Anti-tumor effect of H8L2 antibody in PD-1 HuGEMM MC38-bearing mice

| Groups | Treatment | Tumor size on Day $0^a$ (mm$^3$) | Tumor size on Day $13^a$ (mm$^3$) | TGI (%) | T-C (day) | P value[b] |
|---|---|---|---|---|---|---|
| 3 | H8L2 5 mg/kg | 133.70 ± 17.67 | 133.72 ± 80.59 | 93 | 14 | <0.05 |
| 4 | H8L2 10 mg/kg | 134.16 ± 14.89 | 198.59 ± 122.12 | 90 | >14 | <0.05 |

Note:
[a] data is represented in "mean ± standard error";
[b] the significant difference among groups for tumor size is analyzed by using One-way ANOVA, where Groups 2 to 4 show a statistically significant difference in tumor size compared to Group 1, with P < 0.05.

For the Groups 2 to 4, the T-C values (when the tumor size of mouse reached up to 1000 mm$^3$) were 10 days, 14 days and above 14 days respectively. Further, for the Groups 2 to 4, there were respectively 3 mice, 5 mice and 5 mice left in which the tumor has been regressed completely even for more than one month when the experiment was completed on day 55, refer to Table 5.

TABLE 5

Raw data of tumor volume measurements (mm$^3$)

| groups | ID | 0 | 3 | 6 | 10 | 13 | 17 | 20 | 24 | 27 |
|---|---|---|---|---|---|---|---|---|---|---|
| 01 | 11240 | 91.50 | 215.37 | 266.98 | 613.57 | 1171.37 | 1697.85 | 2643.02 | 4731.76 | 7309.75 |
| 01 | 11243 | 133.90 | 232.18 | 359.57 | 1304.79 | 3568.60 | | | | |
| 01 | 11250 | 80.84 | 109.37 | 143.14 | 271.79 | 466.01 | 894.52 | 1343.39 | 3027.15 | 4135.77 |
| 01 | 11260 | 119.44 | 189.27 | 546.36 | 1410.43 | 2834.20 | 5938.21 | | | |
| 01 | 11275 | 190.55 | 501.32 | 1112.25 | 1864.70 | 3346.82 | | | | |
| 01 | 11282 | 188.05 | 370.78 | 715.45 | 1249.03 | 2433.64 | 4743.60 | | | |
| 01 | 11285 | 154.20 | 312.96 | 497.55 | 884.87 | 1392.71 | 2469.10 | 3736.92 | | |
| 01 | 11286 | 104.36 | 174.07 | 177.68 | 201.64 | 256.00 | 276.76 | 419.35 | 799.84 | 1211.13 |
| 02 | 11248 | 125.08 | 136.50 | 118.99 | 40.80 | 17.53 | 19.47 | 39.80 | 61.94 | 111.33 |
| 02 | 11252 | 153.95 | 209.80 | 191.10 | 41.33 | 44.65 | 0.00 | 0.00 | 0.00 | 0.00 |
| 02 | 11257 | 116.34 | 235.53 | 425.25 | 668.02 | 1331.44 | 2715.30 | 5742.74 | | |
| 02 | 11259 | 257.74 | 414.24 | 200.04 | 59.12 | 0.00 | 0.00 | 0.00 | 0.00 | 0.00 |
| 02 | 11269 | 69.55 | 88.27 | 86.53 | 204.59 | 307.77 | 738.17 | 1166.89 | 2582.80 | 3679.77 |
| 02 | 11270 | 108.74 | 242.30 | 69.38 | 34.57 | 0.00 | 0.00 | 0.00 | 0.00 | 0.00 |
| 02 | 11276 | 155.75 | 255.32 | 322.67 | 193.87 | 97.11 | 66.56 | 0.00 | 0.00 | 93.66 |
| 02 | 11288 | 95.64 | 192.09 | 170.04 | 183.64 | 407.20 | 571.17 | 895.93 | 1662.92 | 2679.55 |
| 03 | 11237 | 116.72 | 115.78 | 45.94 | 12.65 | 0.00 | 0.00 | 0.00 | 0.00 | 0.00 |
| 03 | 11244 | 233.44 | 256.00 | 101.65 | 36.89 | 11.97 | 0.00 | 0.00 | 0.00 | 0.00 |
| 03 | 11245 | 110.01 | 165.51 | 349.87 | 389.56 | 602.01 | 1450.15 | 1927.01 | 4714.50 | 7447.65 |
| 03 | 11247 | 168.78 | 263.15 | 172.85 | 50.65 | 25.35 | 0.00 | 0.00 | 0.00 | 0.00 |
| 03 | 11264 | 150.08 | 194.36 | 148.77 | 151.22 | 0.00 | 0.00 | 0.00 | 0.00 | 0.00 |
| 03 | 11265 | 121.96 | 141.16 | 236.14 | 289.38 | 374.76 | 962.20 | 1562.71 | 2562.71 | 3682.44 |
| 03 | 11281 | 75.20 | 90.90 | 36.06 | 0.00 | 0.00 | 0.00 | 0.00 | 0.00 | 0.00 |
| 03 | 11289 | 93.41 | 109.80 | 73.81 | 66.41 | 55.68 | 127.42 | 205.34 | 340.20 | 604.39 |
| 04 | 11239 | 105.92 | 130.21 | 81.11 | 42.17 | 0.00 | 0.00 | 0.00 | 0.00 | 0.00 |
| 04 | 11249 | 131.09 | 245.40 | 328.17 | 223.28 | 177.06 | 357.63 | 455.97 | 910.09 | 1640.19 |
| 04 | 11251 | 210.58 | 295.98 | 669.19 | 683.19 | 986.53 | 2054.54 | 3341.94 | | |
| 04 | 11254 | 177.51 | 210.00 | 135.76 | 104.35 | 380.87 | 586.87 | 1149.45 | 2010.34 | 2455.90 |
| 04 | 11267 | 145.05 | 246.21 | 110.43 | 42.45 | 17.72 | 0.00 | 0.00 | 0.00 | 0.00 |
| 04 | 11272 | 90.66 | 135.37 | 103.80 | 48.45 | 26.57 | 22.81 | 22.54 | 0.00 | 0.00 |
| 04 | 11277 | 118.78 | 124.35 | 51.15 | 28.47 | 0.00 | 0.00 | 0.00 | 0.00 | 0.00 |
| 04 | 11280 | 93.70 | 184.72 | 101.03 | 32.53 | 0.00 | 0.00 | 0.00 | 0.00 | 0.00 |

| groups | ID | 31 | 34 | 38 | 41 | 45 | 48 | 52 | 55 |
|---|---|---|---|---|---|---|---|---|---|
| 01 | 11240 | | | | | | | | |
| 01 | 11243 | | | | | | | | |
| 01 | 11250 | | | | | | | | |
| 01 | 11260 | | | | | | | | |
| 01 | 11275 | | | | | | | | |
| 01 | 11282 | | | | | | | | |
| 01 | 11285 | | | | | | | | |
| 01 | 11286 | 1774.66 | 2951.53 | 4747.39 | | | | | |
| 02 | 11248 | 248.10 | 525.66 | 1075.55 | 1492.19 | 2249.90 | 3687.06 | | |
| 02 | 11252 | 0.00 | 0.00 | 0.00 | 0.00 | 0.00 | 0.00 | 0.00 | 0.00 |

TABLE 5-continued

| | | \multicolumn{8}{c}{Raw data of tumor volume measurements (mm³)} |
|---|---|---|---|---|---|---|---|---|
| 02 | 11257 | | | | | | | |
| 02 | 11259 | 0.00 | 0.00 | 0.00 | 0.00 | 0.00 | 0.00 | 0.00 |
| 02 | 11269 | 6089.10 | | | | | | |
| 02 | 11270 | 0.00 | 0.00 | 0.00 | 0.00 | 0.00 | 0.00 | 0.00 |
| 02 | 11276 | 176.81 | 298.47 | 508.68 | 600.08 | 1040.07 | 1845.48 | 2366.75 2736.56 |
| 02 | 11288 | 4223.34 | | | | | | |
| 03 | 11237 | 0.00 | 0.00 | 0.00 | 0.00 | 0.00 | 0.00 | 0.00 |
| 03 | 11244 | 0.00 | 0.00 | 0.00 | 0.00 | 0.00 | 0.00 | 0.00 |
| 03 | 11245 | | | | | | | |
| 03 | 11247 | 0.00 | 0.00 | 0.00 | 0.00 | 0.00 | 0.00 | 0.00 |
| 03 | 11264 | 0.00 | 0.00 | 0.00 | 0.00 | 0.00 | 0.00 | 0.00 |
| 03 | 11265 | 4901.56 | | | | | | |
| 03 | 11281 | 0.00 | 0.00 | 0.00 | 0.00 | 0.00 | 0.00 | 0.00 |
| 03 | 11289 | 1050.03 | 1480.22 | 1917.34 | 2547.62 | 4278.69 | | |
| 04 | 11239 | 0.00 | 0.00 | 0.00 | 0.00 | 0.00 | 0.00 | 0.00 |
| 04 | 11249 | 2614.29 | 3839.06 | | | | | |
| 04 | 11251 | | | | | | | |
| 04 | 11254 | 4046.48 | | | | | | |
| 04 | 11267 | 0.00 | 0.00 | 0.00 | 0.00 | 0.00 | 0.00 | 0.00 |
| 04 | 11272 | 0.00 | 0.00 | 0.00 | 0.00 | 0.00 | 0.00 | 0.00 |
| 04 | 11277 | 0.00 | 0.00 | 0.00 | 0.00 | 0.00 | 0.00 | 0.00 |
| 04 | 11280 | 0.00 | 0.00 | 0.00 | 0.00 | 0.00 | 0.00 | 0.00 |

The H8L2 antibody (in respective dosages of 5 mg/kg and 10 mg/kg) shows statistically significant anti-tumor effect on the PD-1 HuGEMM MC38-bearing mouse, which is more effective in tumor complete regression compared to the Keytruda 10 mg/kg treatment group.

Example 10 ADCC and CDC Effects of H8L2 Antibody

The ADCC and CDC effects of the H8L2 antibody prepared in Example 1 were studied, which is described in detail below.

10.1 Determination of Affinity Constant of H8L2 Antibody with FcγRIIIa

Fc receptor FcγRIIIa (also named as CD16a) can bind to the Fc fragment of IgG antibody, thus involving in antibody-dependent cell-mediated cytotoxicity (ADCC). The safety and efficacy of a therapeutic monoclonal antibody will be affected by the binding ability of the monoclonal antibody to the Fc receptor. In this experiment, the affinity constant of H8L2 antibody with FcγRIIIa was detected by using the Fortebio molecular interaction Instrument to evaluate the binding ability of H8L2 antibody to the Fc receptor.

The affinity constant of H8L2 antibody with FcγRIIIa was detected by using the Fortebio Octet molecular interaction Instrument. Specifically, 1 μg/ml FcγRIIIa-Biotin in the PBST buffer was immobilized on the surface of the SA sensor for 300 seconds. The H8L2 antibody in a concentration of 4000 nM was applied to the SA sensor for binding to the FcγRIIIa. After binding for 120 seconds, the PBST buffer was applied to the SA sensor for disassociation, which was kept for 180 seconds. The data was collected with the Fortebio Data Acquisition 7.0 software and analyzed with the Fortebio Data Analysis 7.0 software.

Figure 17:
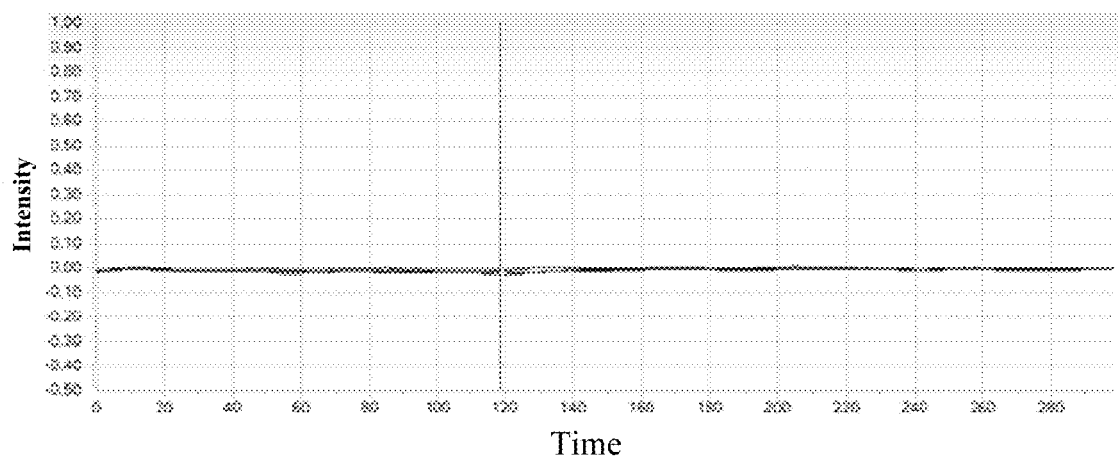
FIG. 17 is a graph showing the detection result of Kinetic characteristic parameters of H8L2 antibody with FcγRIIIa in studies of ADCC and CDC effects according to an embodiment of the present disclosure.

FIG. 17 shows the result, indicating no binding between the H8L2 antibody and FcγRIIIa.

10.2 Determination of Affinity Constant of H8L2 Antibody with C1q

Serum complement C1q can bind to the Fc fragment of IgG antibody, thus involving in complement-dependent cytotoxicity (CDC). The safety and efficacy of a therapeutic monoclonal antibody will be affected by the binding ability of the monoclonal antibody to the serum complement C1q. In this experiment, the affinity constant of H8L2 antibody with the serum complement C1q was detected by using the Fortebio molecular interaction Instrument to evaluate the binding ability of H8L2 antibody to the serum complement C1q.

The affinity constant of H8L2 antibody with the serum complement C1q was detected by using the Fortebio Octet molecular interaction Instrument. Specifically, 100 μg/ml H8L2 antibody in the PBST buffer was immobilized on the surface of the FAB2G sensor for 300 seconds. The serum complement C1q in a concentration from 3.13 to 200 nM was applied to the FAB2G sensor for binding to the H8L2 antibody. After binding for 120 seconds, the PBST buffer was applied to the FAB2G sensor for disassociation, which was kept for 180 seconds. The data was collected with the Fortebio Data Acquisition 7.0 software and analyzed with the Fortebio Data Analysis 7.0 software.

Figure 18:
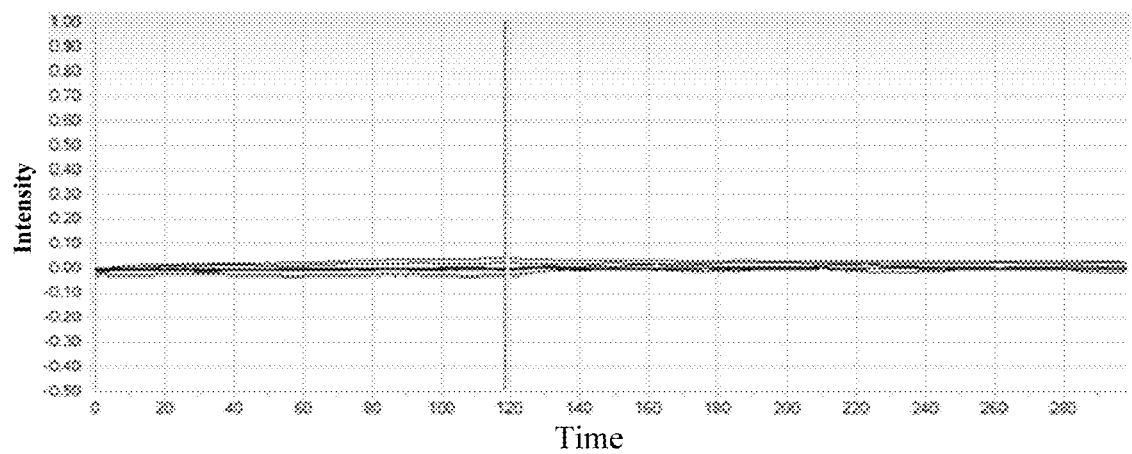
FIG. 18 is a graph showing the detection result of Kinetic characteristic parameters of H8L2 antibody with C1q in studies of ADCC and CDC effects according to an embodiment of the present disclosure.

FIG. 18 shows the result, indicating no binding between the H8L2 antibody and the serum complement C1q.

INDUSTRIAL APPLICABILITY

The monoclonal antibody against PD-1 of the present disclosure exhibits strong binding affinity to FcRn and prolonged serum half-life, as well as strong binding affinity to and good recognition specificity for antigen PD-1. Further, the antibody or antigen-binding fragment thereof is capable of specifically binding to PD-1 or its receptor, thus blocking the PD-1 receptor (such as SHP1/2) related signaling pathway, thereby effectively inhibiting tumor growth.

Although embodiments of the present disclosure have been described in detail, it will be understood by those skilled in the art that various modifications and substitutions can be made in these embodiments as the teaching disclosed, and such the changes are all within the scope of the present disclosure which is given by the appended claims and any equivalents thereof.

In the specification of the present disclosure, the terms "an embodiment", "some embodiments", "a specific embodiment", "an example", "a specific example", "some examples" and the like are intended to refer to particular features, structures, materials or characteristics described by way of example or embodiment are contained in at least one embodiment or example of the disclosure. In this specification, the schematic representation of the above terms does not necessarily refer to the same embodiment or example. Moreover, the particular features, structures, materials or characteristics described may be combined in any suitable manner in one or more embodiments or examples.

What is claimed is:

1. A monoclonal antibody against programmed death-1 (PD-1) or antigen-binding fragment thereof, comprising a neonatal Fc Receptor (FcRn)-binding site comprising the amino acid sequence of SEQ ID NO: 5.

2. The antibody or antigen-binding fragment thereof according to claim 1, comprising:
 a heavy chain comprising the amino acid sequence of SEQ ID NO: 1, and
 a light chain comprising the amino acid sequence of SEQ ID NO: 3.

3. A pharmaceutical composition, comprising:
 a monoclonal antibody or antigen-binding fragment thereof, wherein the monoclonal antibody or antigen-binding fragment thereof comprises a neonatal Fc Receptor (FcRn)-binding site comprising an amino acid sequence of SEQ ID NO: 5.

4. The pharmaceutical composition according to claim 3, wherein the monoclonal antibody or antigen-binding fragment thereof comprises:
 a heavy chain comprising the amino acid sequence of SEQ ID NO: 1, and
 a light chain comprising the amino acid sequence of SEQ ID NO: 3.

5. The pharmaceutical composition according to claim 3, wherein the pharmaceutical composition further comprises an immune-enhancing agent.

6. The pharmaceutical composition according to claim 5, wherein the immune-enhancing agent comprises at least one selected from the group consisting of an anti-cytotoxic T lymphocyte antigen 4 (CTLA-4) antibody, an anti-CD40 antibody, Budesonide and a salicylate.

7. The pharmaceutical composition according to claim 6, wherein the salicylate comprises at least one of sulfasalazine, olsalazine, balsalazide and mesalamine.

* * * * *

UNITED STATES PATENT AND TRADEMARK OFFICE
CERTIFICATE OF CORRECTION

PATENT NO. : 10,858,433 B2  
APPLICATION NO. : 16/510449  
DATED : December 8, 2020  
INVENTOR(S) : Zhang et al.

Page 1 of 1

It is certified that error appears in the above-identified patent and that said Letters Patent is hereby corrected as shown below:

In the Claims

Column 35, Line 51 in Claim 1, "Fe Receptor" should read:
--Fc Receptor--.

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 6

<210> SEQ ID NO 1
<211> LENGTH: 445
<212> TYPE: PRT
<213> ORGANISM: Artificial Sequence
<220> FEATURE:
<223> OTHER INFORMATION: amino acid sequence of heavy chain of H8L2

<400> SEQUENCE: 1

```
Glu Val Gln Leu Val Gln Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
            20                  25                  30

Gly Met Ser Trp Val Arg Gln Ala Pro Gly Lys Gly Leu Asp Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
            85                  90                  95

Ala Arg Gln Lys Gly Glu Ala Trp Phe Ala Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Lys Thr Tyr Thr Cys Asn Val Asp His Lys Pro Ser
    195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Thr Arg Thr Pro Glu
            245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Tyr Arg Val Val Ser Val Leu
290                 295                 300

Thr Pro Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335
```

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Leu Gly Lys
            435                 440                 445

<210> SEQ ID NO 2
<211> LENGTH: 1392
<212> TYPE: DNA
<213> ORGANISM: Artificial Sequence
<220> FEATURE:
<223> OTHER INFORMATION: nucleotide sequence encoding heavy chain of
      H8L2

<400> SEQUENCE: 2

```
atgggatgga gctgtatcat cctcttcttg gtagcaacag ctacaggcgc gcactccgag      60
gtgcagctgg tgcagtctgg cggcggactg gtgcagcccg gcgggtcact gaagctgagc     120
tgcgccgctt ccggcttcac ctttagctcc tacggaatgt cctgggtgcg acaggcaccc     180
gggaaggggc tggactgggt cgctactatc tcaggaggcg ggagagacac ctactatcct     240
gatagcgtca agggccggtt cacaattagc cgggacaaca gcaagaacaa tctgtacctg     300
cagatgaaca gcctgagggc tgaggatact gcactgtact attgtgcccg ccagaagggc     360
gaagcatggt ttgcctattg gggccaggga accctggtca ccgtctcctc agcttccacc     420
aagggcccat ccgtcttccc cctggcgccc tgctccagga gcacctccga gagcacagcc     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac tgtgccctcc agcagcttgg gcacgaagac ctacacctgc     660
aacgtagatc acaagcccag caacaccaag gtggacaaga gagttgagtc caaatatggt     720
cccccatgcc caccatgccc agcacctgag ttcctggggg gaccatcagt cttcctgttc     780 ccccccaaaac ccaaggacac tctcatgatc acccggaccc ctgaggtcac gtgcgtggtg     840
gtggacgtga gccaggaaga cccgaggtc cagttcaact ggtacgtgga tggcgtggag     900
gtgcataatg ccaagacaaa gccgcgggag gagcagttca acagcacgta ccgtgtggtc     960
agcgtcctca ccccctgca ccaggactgg ctgaacggca aggagtacaa gtgcaaggtc    1020
tccaacaaag gcctcccgtc ctccatcgag aaaaccatct ccaaagccaa agggcagccc    1080
cgagagccac aggtgtacac cctgccccca tcccaggagg agatgaccaa gaaccaggtc    1140
agcctgacct gcctggtcaa aggcttctac cccagcgaca tcgccgtgga gtgggagagc    1200
aatgggcagc cggagaacaa ctacaagacc acgcctcccg tgctggactc cgacggctcc    1260
ttcttcctct acagcaggct aaccgtggac aagagcaggt ggcaggaggg gaatgtcttc    1320
tcatgctccg tgatgcatga ggctctgcac gcccactaca cacagaagag cctctcccctg    1380
```
tctctgggta aa                                                        1392

<210> SEQ ID NO 3
<211> LENGTH: 218
<212> TYPE: PRT
<213> ORGANISM: Artificial Sequence
<220> FEATURE:
<223> OTHER INFORMATION: amino acid sequence of light chain of H8L2

<400> SEQUENCE: 3

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Lys Gly Thr Gly Val Pro Ala
    50                  55                  60

Arg Phe Ser Gly Ser Gly Ser Gly Thr Asp Phe Thr Leu Asn Ile Asn
65                  70                  75                  80

Pro Met Glu Glu Asn Asp Thr Ala Met Tyr Phe Cys Gln Gln Ser Lys
                85                  90                  95

Glu Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 4
<211> LENGTH: 711
<212> TYPE: DNA
<213> ORGANISM: Artificial Sequence
<220> FEATURE:
<223> OTHER INFORMATION: nucleotide sequence encoding light chain of
      H8L2

<400> SEQUENCE: 4
atgggatgga gctgtatcat cctcttcttg gtagcaacag ctacaggcgt gcactccgat      60
attgtgctga ctcagagccc tgcttccctg ccgtgtctc caggacagcg agctaccatc     120
acatgcagag catctgagag tgtggacaac tacggaatta gtttcatgaa ttggtttcag     180
cagaagcccg gccagccccc taaactgctg atctatgccg ccagcaacaa gggcaccggg     240
gtgcctgctc gattctcagg aagcggctcc gggacagact ttactctgaa cattaaccca     300
atggaggaaa atgatacagc aatgtacttc tgccagcaga gcaaggaggt gccctggacc     360
tttggcgggg gaacaaagct ggaaatcaaa cgaactgtgg ctgcaccatc tgtcttcatc     420

```
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg t             711
```

<210> SEQ ID NO 5
<211> LENGTH: 327
<212> TYPE: PRT
<213> ORGANISM: Artificial Sequence
<220> FEATURE:
<223> OTHER INFORMATION: FcRn-binding site of the heavy chain constant
      region of monoclonal antibody against PD-1

<400> SEQUENCE: 5

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Thr Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Pro Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Ala His Tyr Thr Gln Lys Ser
305                 310                 315                 320

Leu Ser Leu Ser Leu Gly Lys
                325

<210> SEQ ID NO 6
<211> LENGTH: 1038
<212> TYPE: DNA
<213> ORGANISM: Artificial Sequence
<220> FEATURE:
<223> OTHER INFORMATION: nucleic acid sequence encoding FcRn-binding
      site of heavy chain constant region of antibody

<400> SEQUENCE: 6
aagggcgaag catggtttgc ctattggggc cagggaaccc tggtcaccgt ctcctcagct      60
tccaccaagg gcccatccgt cttcccctg gcgccctgct ccaggagcac ctccgagagc     120
acagccgccc tgggctgcct ggtcaaggac tacttccccg aaccggtgac ggtgtcgtgg    180
aactcaggcg ccctgaccag cggcgtgcac accttcccgg ctgtcctaca gtcctcagga    240
ctctactccc tcagcagcgt ggtgactgtg ccctccagca gcttgggcac gaagacctac    300
acctgcaacg tagatcacaa gcccagcaac accaaggtgg acaagagagt tgagtccaaa    360
tatggtcccc catgcccacc atgcccagca cctgagttcc tggggggacc atcagtcttc    420
ctgttccccc caaaacccaa ggacactctc atgatcaccc ggacccctga ggtcacgtgc    480
gtggtggtgg acgtgagcca ggaagacccc gaggtccagt tcaactggta cgtggatggc    540
gtggaggtgc ataatgccaa gacaaagccg cgggaggagc agttcaacag cacgtaccgt    600
gtggtcagcg tcctcacccc cctgcaccag gactggctga acggcaagga gtacaagtgc    660
aaggtctcca acaaaggcct cccgtcctcc atcgagaaaa ccatctccaa agccaaaggg    720
cagccccgag agccacaggt gtacaccctg cccccatccc aggaggagat gaccaagaac    780
caggtcagcc tgacctgcct ggtcaaaggc ttctacccca gcgacatcgc cgtggagtgg    840
gagagcaatg ggcagccgga gaacaactac aagaccacgc ctcccgtgct ggactccgac    900
ggctccttct cctctacag caggctaacc gtggacaaga gcaggtggca ggaggggaat    960
gtcttctcat gctccgtgat gcatgaggct ctgcacgccc actacacaca gaagagcctc   1020
tccctgtctc tgggtaaa                                                 1038
```